(12) United States Patent
duBois

(10) Patent No.: US 11,730,366 B2
(45) Date of Patent: Aug. 22, 2023

(54) PNEUMATIC PRESSURE PROBE

(71) Applicant: Robert Ogden Crane duBois, Glen Arm, MD (US)

(72) Inventor: Robert Ogden Crane duBois, Glen Arm, MD (US)

(73) Assignee: OcuFLOW, Inc., Glen Arm, MD (US)

(*) Notice: Subject to any disclaimer, the term of this patent is extended or adjusted under 35 U.S.C. 154(b) by 760 days.

(21) Appl. No.: 16/602,509

(22) Filed: Oct. 21, 2019

(65) Prior Publication Data
US 2021/0113082 A1    Apr. 22, 2021

(51) Int. Cl.
*A61B 3/16* (2006.01)
*G01L 19/06* (2006.01)
*A61B 3/00* (2006.01)

(52) U.S. Cl.
CPC ............ *A61B 3/16* (2013.01); *A61B 3/00* (2013.01); *G01L 19/0609* (2013.01); *G01L 19/0672* (2013.01)

(58) Field of Classification Search
CPC .................................... A61B 3/00; A61B 3/16
See application file for complete search history.

(56) References Cited

U.S. PATENT DOCUMENTS

| | | |
|---|---|---|
| 3,974,932 A | 8/1976 | Faulstich |
| 4,519,614 A | 5/1985 | Garner |
| 4,883,056 A | 11/1989 | Langham |
| 5,857,969 A | 1/1999 | Massey et al. |
| 6,010,478 A | 1/2000 | Bellhouse et al. |
| 2017/0245751 A1 | 8/2017 | DuBois et al. |
| 2018/0296090 A1* | 10/2018 | McCafferty ............ A61B 3/107 |

FOREIGN PATENT DOCUMENTS

| | | | |
|---|---|---|---|
| EP | 315329 A * | 5/1989 | ............ A61B 3/16 |
| JP | 6847614 B2 * | 3/2021 | |
| WO | WO-2021205310 A1 * | 10/2021 | |

OTHER PUBLICATIONS

Whitacre et al., "Sources of Error with Use of Goldmann-type Tonometers," Survey of Ophthalmology, 1993; 38(1):1-30.
Walker and Litovitz, "An Experimental and Theoretical Study of the Pneumatic Tonometer," Exp. Eye Res. 1972; 13:14-23.
Walker & Langham, "Pneumatic Applanation Tonometer Studies, III. Analysis of the Floating Tip Sensor," Exp.Eye Res. 1975.; 20:167-172.
Walker, Compton & Langham, "Pneumatic Applanation Tonometer Studies IV.Analysis of Pulsatile Response,"Exp.EyeRes1975; 20:245-253.

(Continued)

*Primary Examiner* — Andre J Allen
(74) *Attorney, Agent, or Firm* — Wilson Sonsini Goodrich & Rosati

(57) ABSTRACT

A pneumatic pressure probe comprises an orifice tube extending through a plastic bushing that seals a pressure chamber. The orifice tube has a passage shaped substantially like a converging/diverging de Laval nozzle to reduce turbulence in fluid flow through the probe. More laminar fluid flow reduces noise and inaccuracy in the output of the probe. Laminar flow also reduces user dependent results. The plastic bushing and a specially shaped probe tip reduce extraneous fluid leakages from the probe.

21 Claims, 34 Drawing Sheets

(56) References Cited

OTHER PUBLICATIONS

Bhutto et al., "Understanding Age-Related Macular Degeneration . . . ," Molecular Aspects of Medicine Aug. 2012; 33(4):295-3178.
McLeod, et al.,"Relationship between RPE and Choriocapillaris in AMD, "InvestOphthalmolVisSci., 2009; 50:4982-4991.
Cherecheanu, et al., "Ocular Perfusion Pressure & Ocular Blood Flow in Glaucoma," Curr Opin Pharmacol, Feb. 2013; 13(1):36-42.
Flammer et al., "The Impact of Ocular Blood Flow in Glaucoma," Prog Ret Res, 2002;21:359-393.
Grieshaber, et al. "Blood Flow in Glaucoma," Curr Opin Ophthalmol, 2005;16:79-83.
Marangoni, et al., "Subfoveal Choroidal Blood Flow&Central Retinal Function in Early Glaucoma," Acta Ophthalmol. 2012;90:e288-e294.
Lutty, "Effects of Diabetes on the Eye," IOVS. 2013 Dev;54(14):81-87.
Langham, "The Application of the Alcon Applanation Pneumatonograph to Clinical Opthalmology," Alcon Laboratories 1974, pp. 1-66.
FDA 510(k) Application Details—K863217.
FDA 510 (k) Premarket Notification—K002395.
FDA 510(k) Notification #K772130.
FDA 510(k) Notification K873422.
FDA 510(k) Summary K023245.
FDA 510(k) Summary K970887.
FDA 510(k) No. K010998.

\* cited by examiner

Detail C

PNEUMATIC PRESSURE PROBE

TECHNICAL FIELD

This application relates to the field of ophthalmology. More specifically, this application relates to pneumatic tonography and ocular blood flow measurement, most specifically, to a pneumatic pressure probe useful in practicing pneumatic tonography and making ocular blood flow measurements.

BACKGROUND

Tonometry, sometimes referred to as tonography, is the science of intraocular pressure (IOP) measurement based on the resistance of the cornea to a certain amount of force applied to the cornea. IOP arises as a result of blood flow from the ophthalmic artery, which is the first branch of the internal carotid artery before the brain. The ophthalmic artery nourishes the eye by supplying blood to the optic nerve, the choroid, and the retina.

Measurements of IOP are used to diagnose and monitor blinding eye diseases. In addition to indicating eye disease, IOP can also indicate perturbations in the heart and blood vessels feeding the brain, as ocular blood pressure reflects blood flow from the heart to the internal carotid artery, which feeds the brain and the eye.

IOP is most commonly measured using the Goldmann applanation tonometer (Whitacre, 1993). The Goldmann device measures the amount of force required to flatten or applanate a portion of the cornea using a small pressure probe. The IOP acts in opposition to the applied force, and is thus equivalent to the applied force. Other similar devices are the Perkins Hand-Held Field Tonometer, and the Draeger and Mackay-Marg tonometer, which operate on the same principles. However, conventional applanation tonometry is limited to static measurements averaged over time. The tonometric device described in this application can record time-resolved dynamic measurements. In addition, the device described in this application provides information about ocular blood flow and hemodynamics, which cannot be provided by traditional applanation tonometers.

Prior art pneumatic tonometry instruments functioned primarily as applanation tonometers with some aspects of indentation tonometry. Those tonometers consisted of a 3.06 mm diameter plastic disc on a probe tip attached to the end of a piston that rides on a stream of air. The disc was covered by a 6 mm. diameter, silicone membrane. The cornea is applanated by the plastic disc/silicone membrane unit on the probe tip. When the cornea is flattened by the probe tip, the pressure pushing forward on the probe tip is equal to the IOP. The device measures the pressure within the system at this point and the pressure in mm Hg is displayed. The readings correlate well with Goldmann applanation tonometry within normal IOP ranges. Because the pneumatic flow feeding the floating probe tip could not be precisely regulated for instantaneous compensation of the pulsatile nature of the IOP, the force used to applanate the eye caused a slight indentation effect. These prior versions pneumatic tonometer include the Alcon Pneumatic Applanation Tonometer (pre-Amendments FDA), the Biorad-Digilab-Modular One Applanation Tonometer (K863217) marketed as the Mentor Pneumatonometer (K002395), and the Reichert Model 30T Pneumatonometer. Pneumatonometers that measure IOP and ocular blood flow include the Digilab Ocular Cerebral Vascular Monitor (K772130), the OBF Model 115 Computer Tonometer System (K873422), the Paradigm Blood Flow Analyzer Model 408-100-01 (K023245) and the Langham Ocular Blood Flow Tonograph/Tonometer, Model 201 (K010998). The "K" numbers above are the FDA 510(k) clearance numbers. The fundamental operational aspects and function of the pneumatic tonometer in each of these devices is substantially equivalent.

All of these predicates were cleared by the FDA as substantially equivalent and thus considered to have virtually indistinguishable fundamental scientific technology and functionality. While the literature gives substantial descriptions and analyses of the operating principles of pneumatic pressure probes (Walker and Litovitz 1972, Walker, Litovitz, and Langham 1972, Walker and Langham, 1975, Walker, Compton, and Langham et al. 1975, Langham U.S. Pat. No. 4,883,056, and Massey et al. U.S. Pat. No. 5,857,969) for the measurement of ocular blood flow, these devices have all produced unsatisfactory blood flow measurement, as the acquired LOP measurements are inaccurate, unstable, and/or not repeatable, the results being heavily dependent on the skill of the operator. Most probes listed above are no longer on the market for those reasons.

Recent literature has reported that measurement of the choroidal circulation, which accounts for 85-90% of ocular blood flow, is integral to the early monitoring and management of the three most common blinding conditions. These include age-related macular degeneration (Bhutto, 2012, McLeod, 2009), glaucoma (Cherecheanu et al., 2013, Flammer et al., 2002, Grieshaber & Flammer, 2005, and Marangoni et al., 2012) and diabetic retinopathy (Lutty, 2013). Early detection of choroidal blood flow abnormalities is critical for slowing the progression and improving the prognosis of these diseases through preventative treatments. There thus is a long-felt but unmet need for an easy to use device that provides accurate, stable, and repeatable measurements of IOP and ocular blood flow.

BIBLIOGRAPHY

1. Whitacre, M, Stein, R. Sources of error with use of Goldmann-type tonometers. *Surv Opthalmol*, 1993; 38(1):1-30.
2. Walker, R E, Litovitz, T L, An Experimental and Theoretical Study of the Pneumatic Tonometer, *Exp. Eye Res.* 1972; 13:14-23.
3. Walker, R E, Litovitz, T L. Langham, M E, Pneumatic Applanation Tonometer Studies, II. Rabbit Cornea Data, *Exp. Eye Res.* 1972; 13:187-193.
4. Walker, R E, Langham, M E. Pneumatic applanation tonometer studies. III. Analysis of the floating tip sensor. *Exp Eye Res,* 1975; 20:167-172.
5. Walker, R E, Compton, G A, Langham, M E. Pneumatic applanation tonometer studies. IV. Analysis of pulsatile response. *Exp Eye Res,* 1975; 20:245-253.
6. Bhutto, I, Lutty, G A. Understanding age-related macular degeneration (AMD): Relationships between the photoreceptor/retinal pigment epithelium/Bruch's membrane/ choriocapillaris complex. *Mol As-pects Med,* 2012 August; 33(4):295-317.
7. McLeod, D S, Grebe, R, Bhutto, I, Merges, C, Baba, T, Lutty, G A. Relationship between RPE and choriocapillaris in age-related macular degeneration. *Invest Ophthalmol Vis Sci,* 2009; 50:4982-4991.
8. Cherecheanu, A P, Garhofer, G, Schmidl D, Werkmeister R, Schmetterer L: Ocular perfusion pressure and ocular blood flow in glaucoma. Curr Opin Pharmacol. 2013 February; 13(1):36-42. doi: 10.1016/j.coph.2012.09.003. Epub 2012 Sep. 23.

9. Flammer, J, Orgul, S, Costa, V P, Orzalesi, N, Kriegelstein, G K, Serra, L M, Renard, J-P, Stefánsson, E. The impact of ocular blood flow in glaucoma. *Prog Ret Res,* 2002; 21:359-393.
10. Grieshaber M D, Flammer, F. Blood flow in glaucoma. *Curr Opin Ophthalmol,* 2005; 16:79-83.
11. Marangoni, D, Falsini, B, Colotto, A, Salgarello, T, Anselmi, G, Fadda, A, DiRenzo, A D, Campos, E C, Riva, C E. Subfoveal choroidal blood flow and central retinal function in early glaucoma. *Acta Ophthalmol.* 2012; 90:e288-294.
12. Lutty, G A. Effects of diabetes on the eye. IOVS. 2013 Dev; 54(14):81-87.
13. Langham U.S. Pat. No. 4,883,056.
14. Massey et al. U.S. Pat. No. 5,857,969.

SUMMARY

The inaccuracy, instability, and non-repeatability of measurements made by prior pneumatic tonometers are substantially reduced by providing a specially shaped orifice tube in the fluid flow path through a pressure probe used to measure IOP in pneumatic tonometers. The accuracy, stability, and repeatability of those measurements are further improved by providing a special plastic bearing in the pressure probe and a specially shaped probe tip that prevent extraneous leakage of pneumatic fluid from the pressure probe.

DETAILED DESCRIPTION

Figure 1:
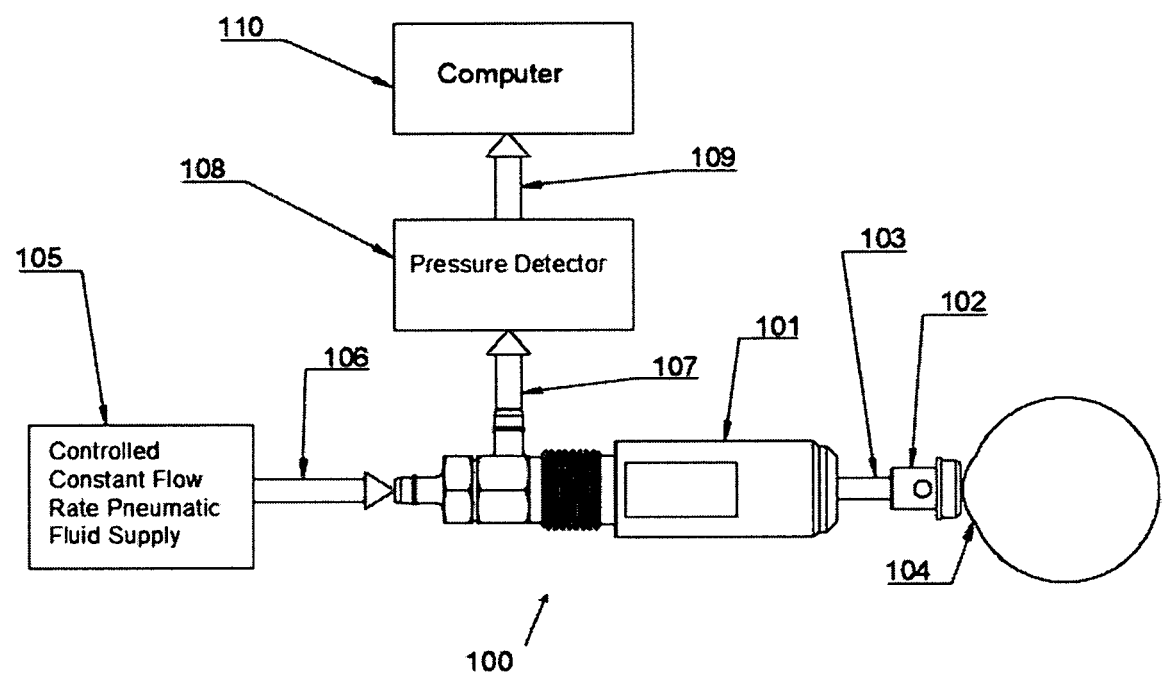
FIG. 1 is a schematic diagram showing an example of a pneumatic pressure probe in accordance with the invention used in a representative intraocular blood pressure and blood flow measurement device.

FIG. 1 shows an example of a pressure probe 100 in accordance with the invention in an illustrative ocular blood flow measurement system. The probe 100 comprises a probe body 101 out of which extends a piston in the form of a probe tip and shaft assembly. The probe tip and shaft assembly comprises a probe tip 102 attached to a rod 103 that slides axially into and out of the probe housing 101. The distal end of the probe tip 102 is pressed against the cornea of an eye 104 to take pressure readings from which intraocular pressure and ocular blood flow can be derived. A pneumatic pressure source 105 supplies pressurized pneumatic fluid at a preferably constant flow rate to the pressure probe 100 through an input line 106. The pressurized fluid delivered to the probe interacts with the intraocular pressure fluctuations in the eye to result in a corresponding fluctuation in fluid pressure in the probe 100 that tracks the time-resolved, pulsatile IOP variation in the eye 104. These probe pressure fluctuations are directed to a detection line 107 connected to a pressure detector 108 that delivers an electrical signal representing probe pressure over communication line 109 to a computer 110. The computer 110 computes the IOP in the eye 104 from the probe pressure. The computer 110 also computes various ocular blood flow parameters useful in diagnosis and treatment of ocular, cerebral, and systemic disease. An illustrative ocular blood flow measurement system is described in published US Patent Application US2017/0245751A1.

Figure 2A:
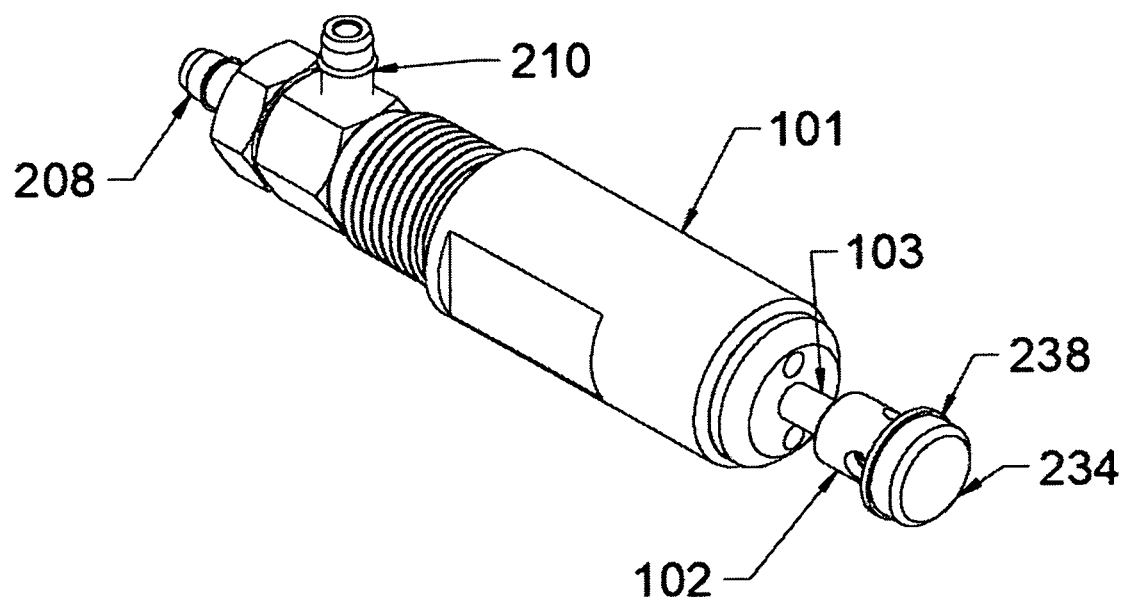
FIG. 2A is a detailed perspective view of the pneumatic probe shown in FIG. 1.
Figure 2B:
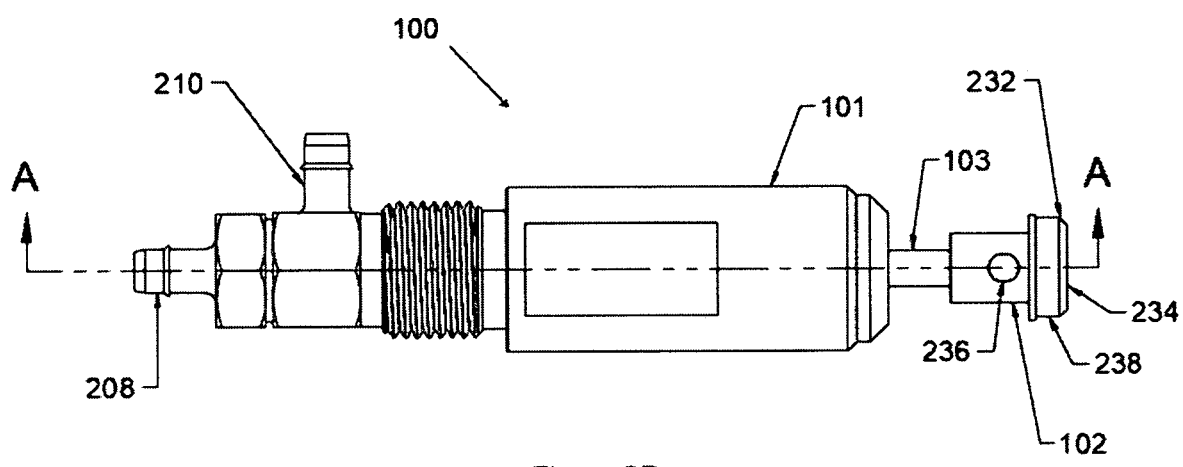
FIG. 2B is a side view of the pneumatic probe shown in FIG. 2A.
Figure 2C:
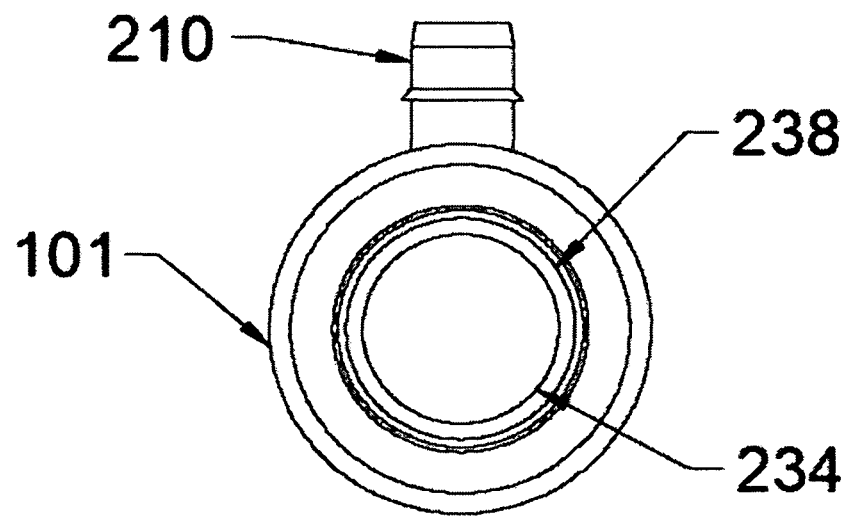
FIG. 2C is a front view of the pneumatic probe shown in FIG. 2A.
Figure 2D:
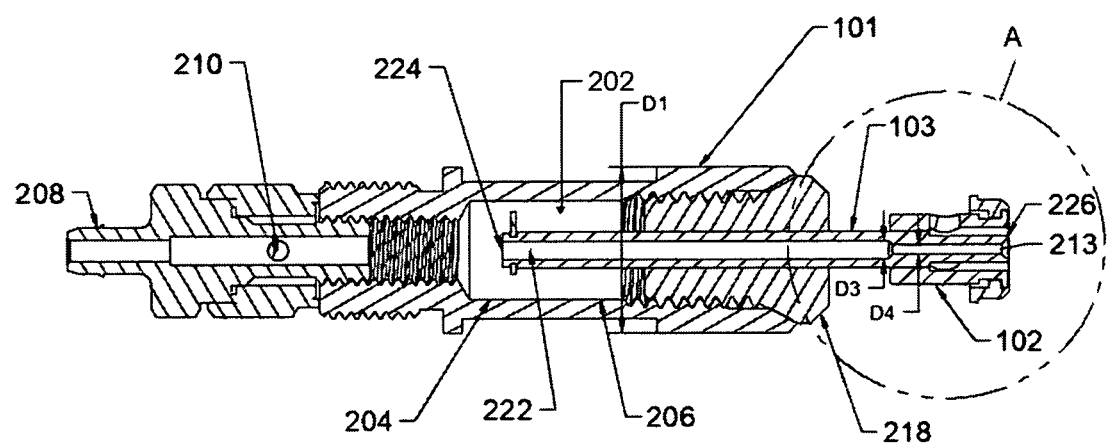
FIG. 2D is a cross sectional diagram of the pneumatic probe of FIG. 2A taken along line A-A in FIG. 2B.
Figure 2E:
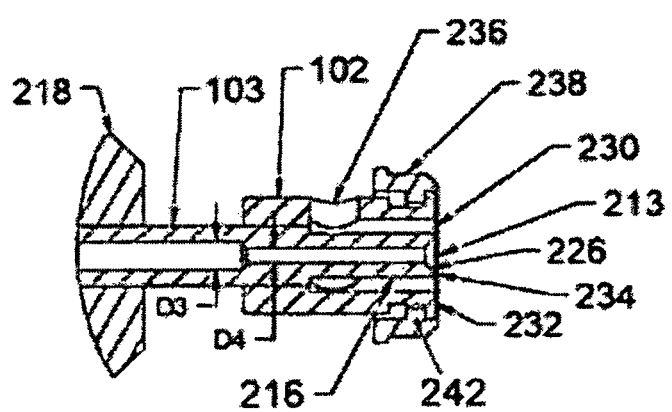
FIG. 2E is a magnification of the region inside circle A in FIG. 2D.
Figure 3A:
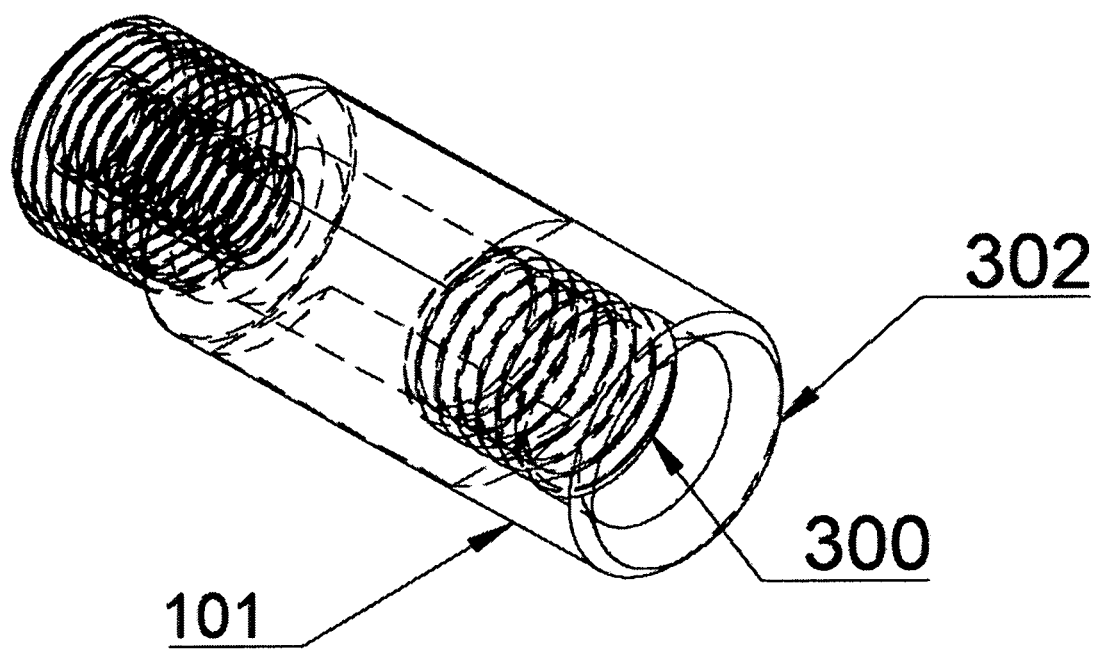
FIG. 3A is a perspective view of the probe housing shown in FIGS. 2A-2D.
Figure 3B:
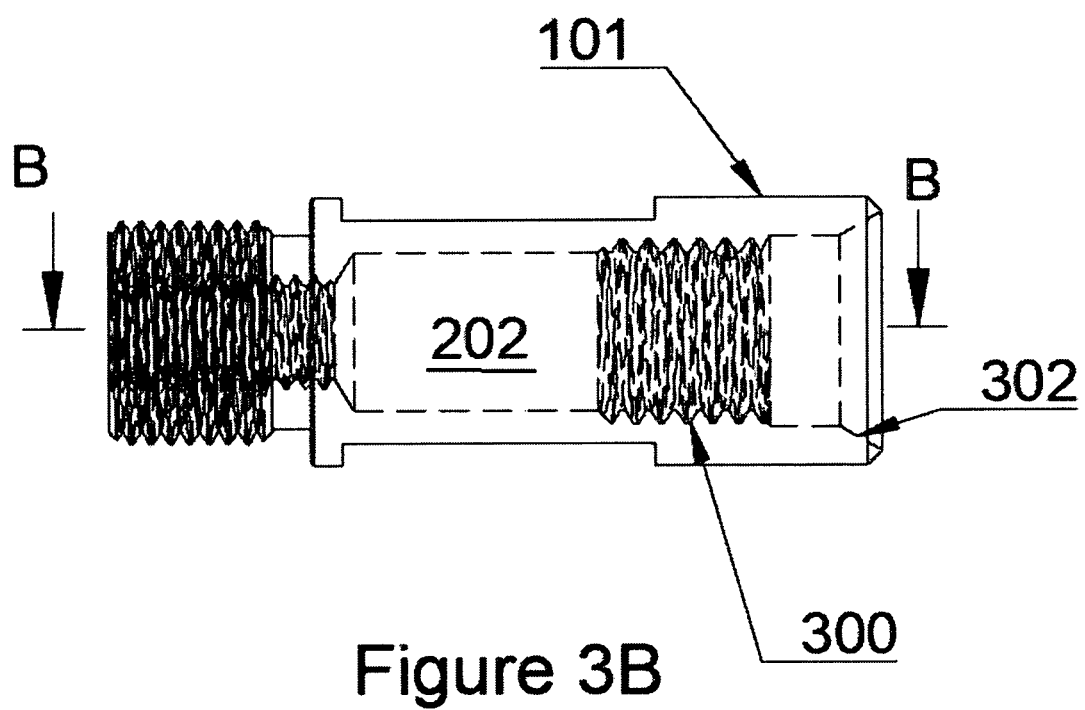
FIG. 3B is a side view of the probe housing of FIG. 3A.
Figure 3C:
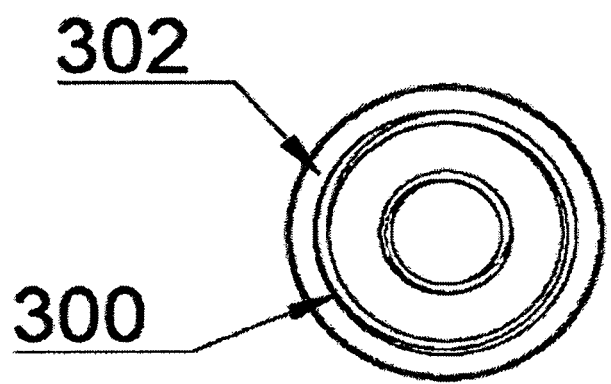
FIG. 3C is a front view of the probe housing of FIG. 3A.
Figure 3D:
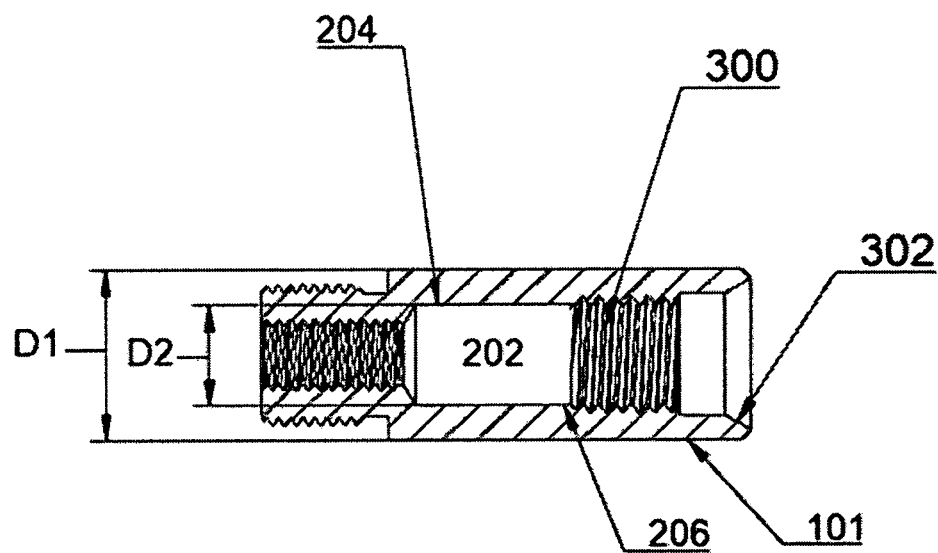
FIG. 3D is a cross sectional view of the probe housing of FIG. 3B taken along line B-B in FIG. 3B.
Figure 4A:
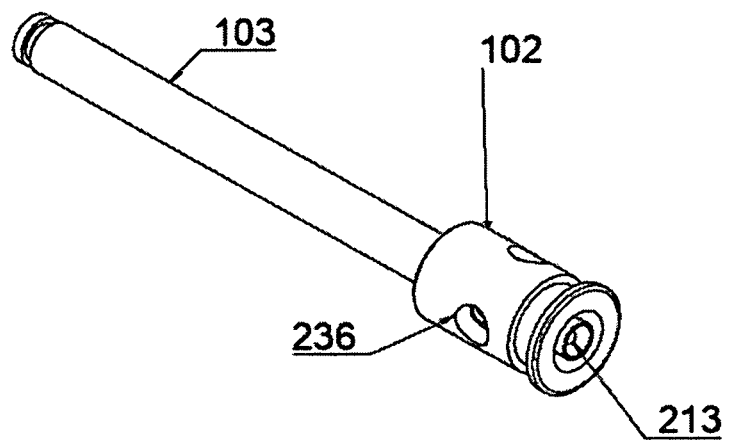
FIG. 4A is a perspective view of the probe tip and shaft assembly shown in FIGS. 2A-2D.
Figure 4B:
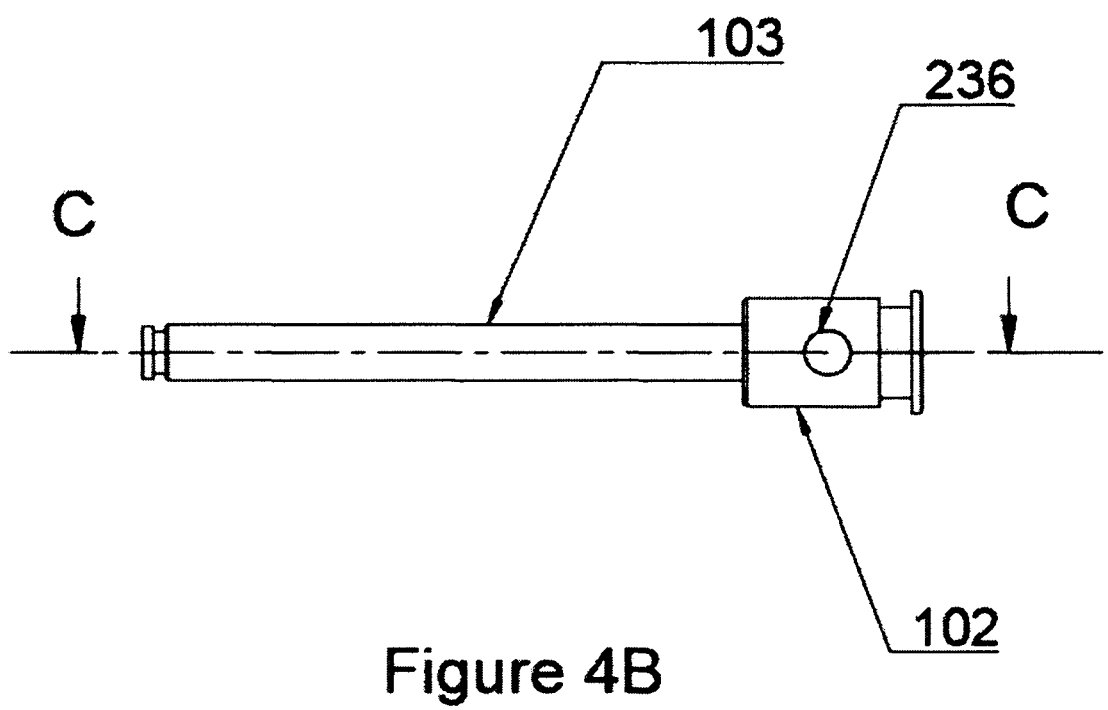
FIG. 4B is a side view of the probe tip and shaft assembly of FIG. 4A.
Figure 4C:
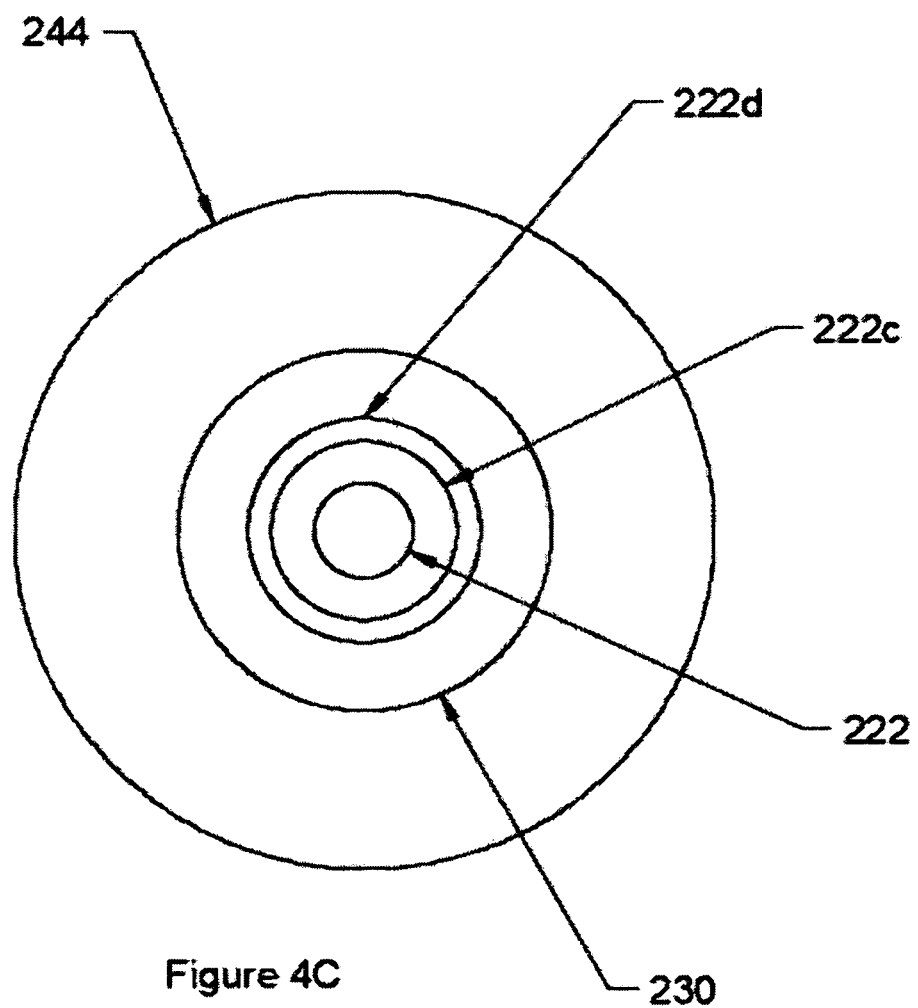
FIG. 4C is a front view of the probe tip and shaft assembly of FIG. 4A.
Figure 4D:
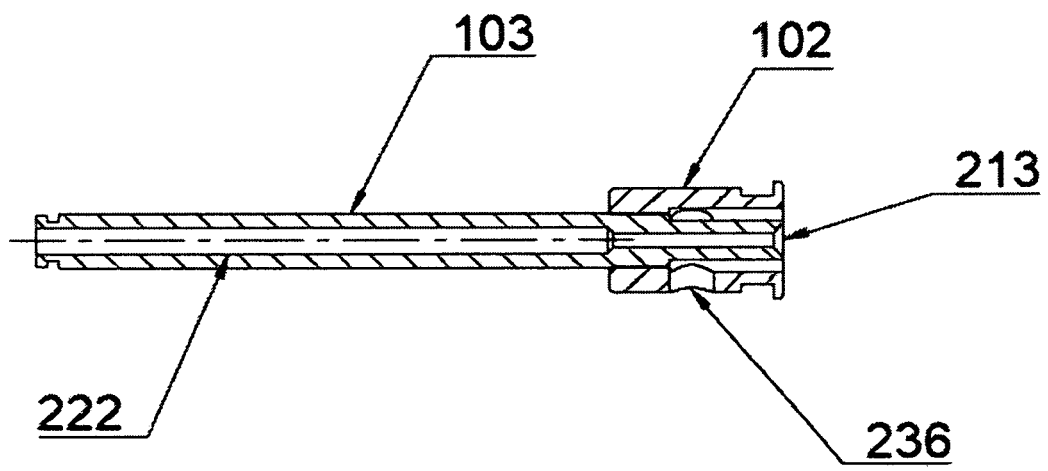
FIG. 4D is a cross sectional view of the probe tip and shaft assembly of FIG. 4B taken along line C-C in FIG. 4B.

FIGS. 2A-2E show the details of the pressure probe 100 in FIG. 1. The probe 100 comprises a hollow elongated housing 101 having an outside diameter D1. See FIGS. 2D and 3D. The housing 101 encloses a generally cylindrical pressure chamber 202 symmetrically disposed along the central axis of the housing 101 and having an inside diameter D2. See FIGS. 3A-3D. As shown in FIG. 2D, the pressure chamber 202 has a proximal end 204 and a distal end 206 inside the housing 101. Fittings for an inlet port 208 and a detection port 210 are screwed into the proximal end of the housing 101. The inlet port 208 is adapted to admit air from the pneumatic pressure source 105 into the proximal end 204 of the pressure chamber 202. The detection port 210 is adapted to communicate with the pressure detector 108 that measures the air pressure in the chamber 202. The fittings for the inlet port 208 and the detection port 210 close the proximal end of the housing 101.

As shown most clearly in FIGS. 3A-3D, the housing 101 has a threaded section 300 and a female conical section containing a slanted sidewall 302 at the distal end of the housing 101. The threaded section 300 and the female conical section with slanted side wall 302 are adapted to receive a corresponding male conical section with slanted side wall 702 located on a cylindrical plastic bearing or bushing 218, described below. The bushing 218 is adapted to be screwed into the threaded section 300. The female slanted sidewall 302 is configured to mate with the male slanted sidewall 702 to seal the distal end of the pressure chamber 202. See FIGS. 3A-3D and 7A-7D. As shown in FIGS. 7A-7D, the bushing 218 also has a cylindrical passage 704 extending along axis 706 through which the rod 103 extends.

As shown, for example, in FIG. 2D, the shaft 103 axially slides with respect to the housing 101 through the cylindrical bearing or bushing 218 screwed into the distal end of the housing 101 Preferably, the bushing 218 is made of a flexible material that effectively seals the space between the probe shaft 103 and the housing 101 so that air escapes from the pressure chamber 202 only through the passage 222 in the probe tip shaft 103 described below. At the same time, the material of the bushing 218 should exhibit low coefficient of friction so that the probe shaft 103 easily slides through the bushing 218. These two requirements are met by an illustrative polytetrafluoroethylene (PTFE) material, preferably, a Rulon® brand PTFE material, such as Rulon® 641 medical grade PTFE material.

Figure 7A:
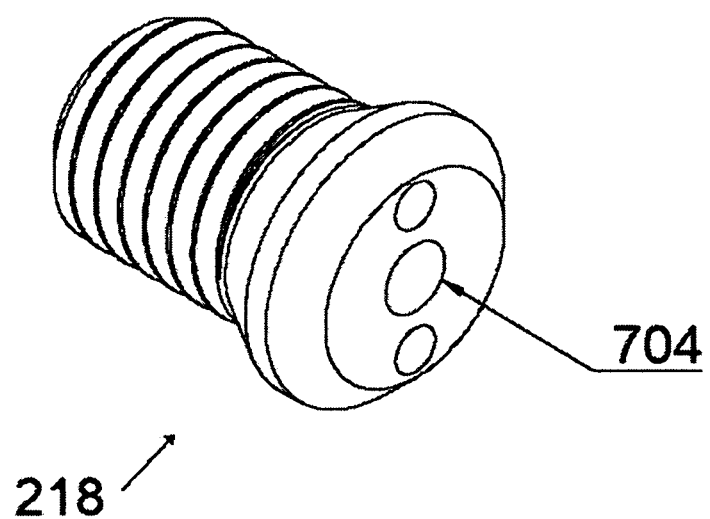
FIG. 7A is a perspective view of the bushing shown in FIGS. 2A-2D.
Figure 7B:
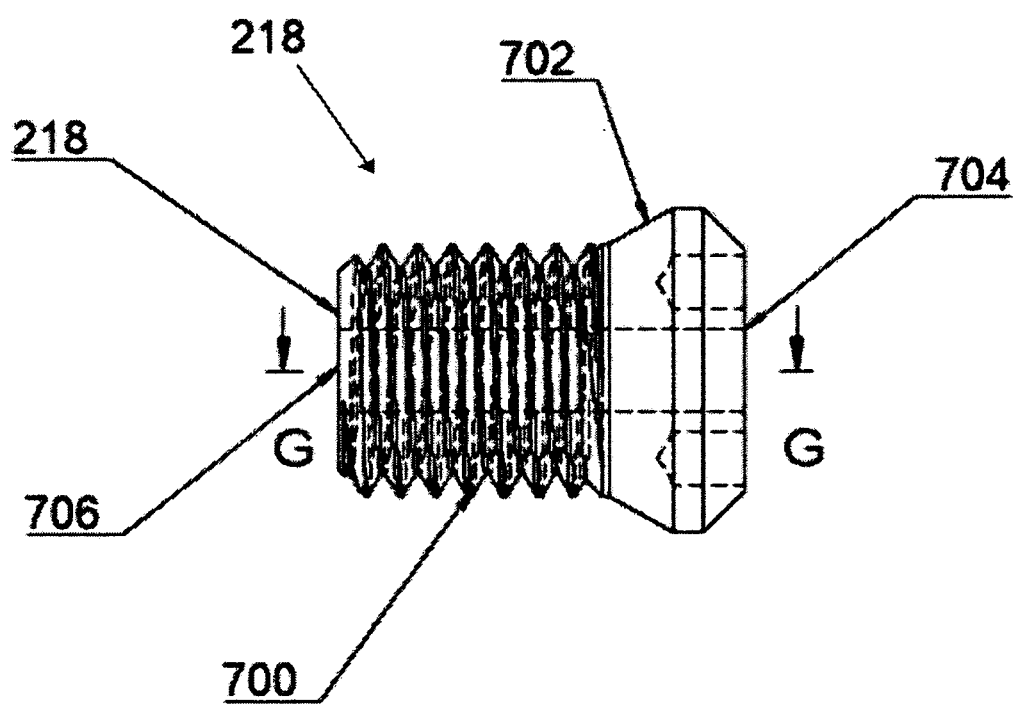
FIG. 7B is a side view of the bushing of FIG. 7A.
Figure 7C:
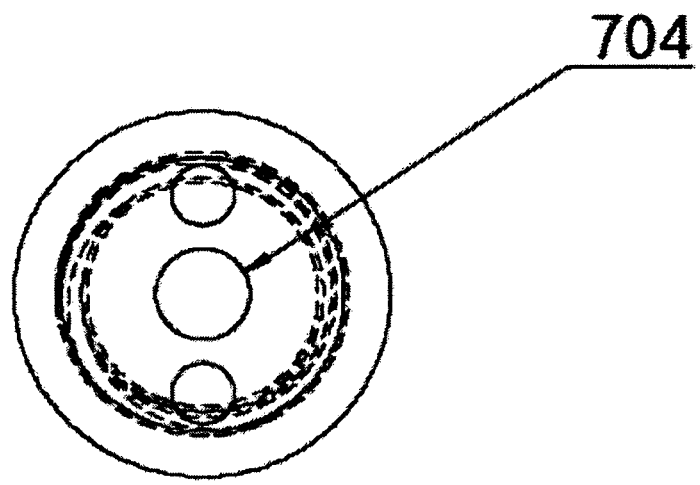
FIG. 7C is a front view of the bushing of FIG. 7A.
Figure 7D:
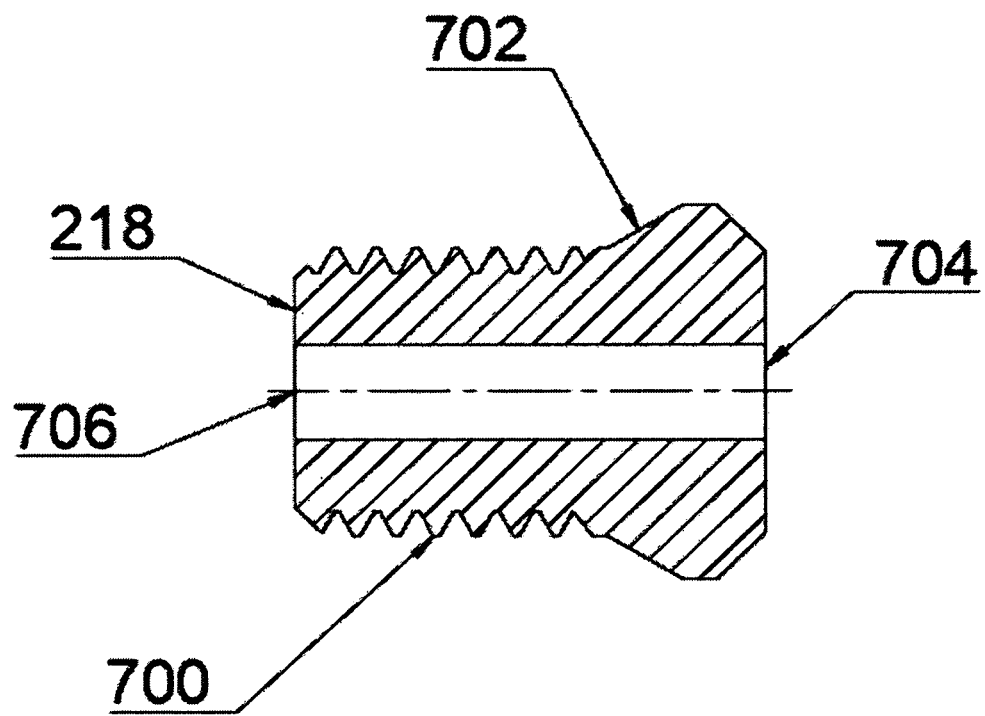
FIG. 7D is a cross sectional view of the bushing of FIG. 7B taken along line G-G in FIG. 7B.
Figure 8A:
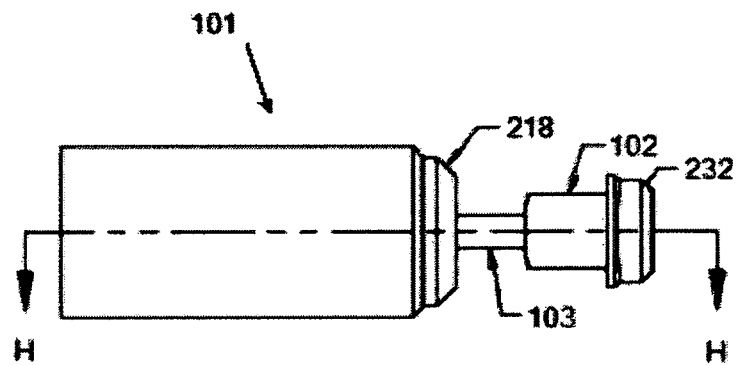
FIG. 8A is a side view of the probe tip, probe shaft, and bushing assembly screwed into the probe housing shown in FIG. 2B.
Figure 8B:
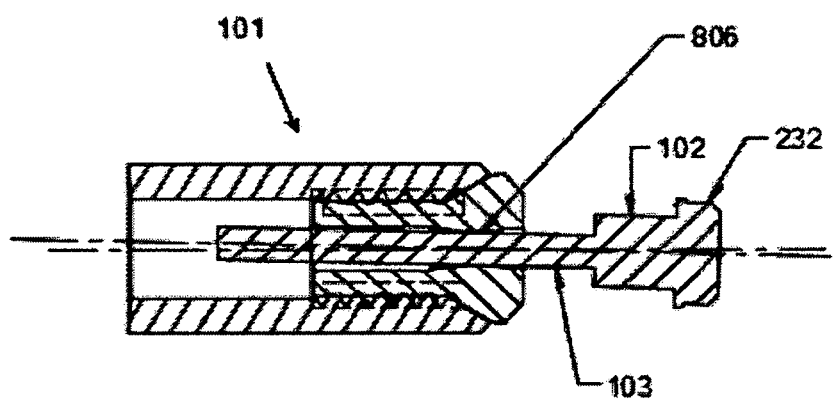
FIG. 8B is a schematic cross section of the probe tip, probe shaft, and bushing assembly taken along line H-H in FIG. 8A that illustrates the behavior of the bushing with respect to the probe shaft.

The Rulon® bushing 218 screws into the housing 101. The slanted portion 702 of the bushing 218 is urged against slanted portion 302 of the housing 101, which causes the bushing 218 to squeeze the shaft 103 with increased force in a narrow band near the axial location of the slanted portion 302 of the housing 200 (FIG. 3A) and the slanted portion 702 of the bushing 218 (FIGS. 7B, 7D, and 8B). The amount of the increased force is determined by how tightly the bushing 218 is screwed into the housing 101. The bushing 218 thus acts as a kind of collet. A collet type of bushing has a geometric advantage over traditional bushings. It is conical, and in effect it grasps the shaft at one end, while leaving the other end relatively loosely held by a concentric passage. This means the shaft 103 can angularly pivot about the area on the shaft 103 grasped by the bushing 218 toward the distal end of the shaft 103, essentially wagging the other end in the looser hole. In the prior art, the shaft rattles around in an air bearing, allowing it to bind like a stuck kitchen drawer and allows pneumatic fluid to leak from the pressure chamber 202. The inner shaft end in this invention merely glances off the inner circumference of the bushing 218, which acts as a loose guide on one end. This has a dramatic effect on the mechanics of the probe. As shown in FIG. 8B, the funnel shaped end of the bushing 218 compresses inward against the shaft 103 with a greater force compared to the force exerted elsewhere along the shaft 103. This is represented in FIG. 8B by a curved inward bulge 806 in the wall surrounding the outer end of the shaft 103. Although there is really no actual bulge in an actual device, because the shaft 103 is a solid rod, it is shown in the FIG. 8B to illustrate the location of increased force on the shaft 103 caused by the interaction of slanted surfaces 302 and 702. This acts like a ball joint around the cylindrical shaft 103, which remains relatively loose elsewhere. Thus a relatively loose fit at the rear is established, while tight squeeze is established at the bulge, which guides the shaft 103 and seals the gap between the shaft 103 and the bushing 218. At the same time, a superior low and effective coefficient of friction is maintained allowing the shaft 103 to move smoothly into and out of the pressure chamber 202.

The seal by the bushing 218 in a probe 100 in accordance with this invention is uniquely designed to constrict closely about the sliding shaft 103 when tightened in the threaded body 101. The sliding shaft 103 is constrained from lateral motion estimated to be less than about 0.001", while axial motion remains unrestricted. Rulon 641's extremely low coefficient of friction specified to be between 0.10 and 0.3 facilitates this axial motion. Although axial movement of the shaft 103 is substantially unrestricted, airflow through the region between the shaft 103 and the bushing 218 is substantially reduced in a probe in accordance with this invention compared to prior probes.

Binding of a shaft in a hole occurs regularly in prior art, causing unreliable performance and lack of repeatability. The shaft/seal combination in accordance with this invention cannot bind. The constricted area 806 shown in FIG. 8B acts as a ball joint around shaft 103. Prior probes will extend under their own weight only on the axis of the shaft being fully vertical. The probe in accordance with this invention will extend under it's own weight when the probe is tilted, estimated to be approximately no more than about 20 degrees from horizontal along the axis of the shaft.

Figure 5A:
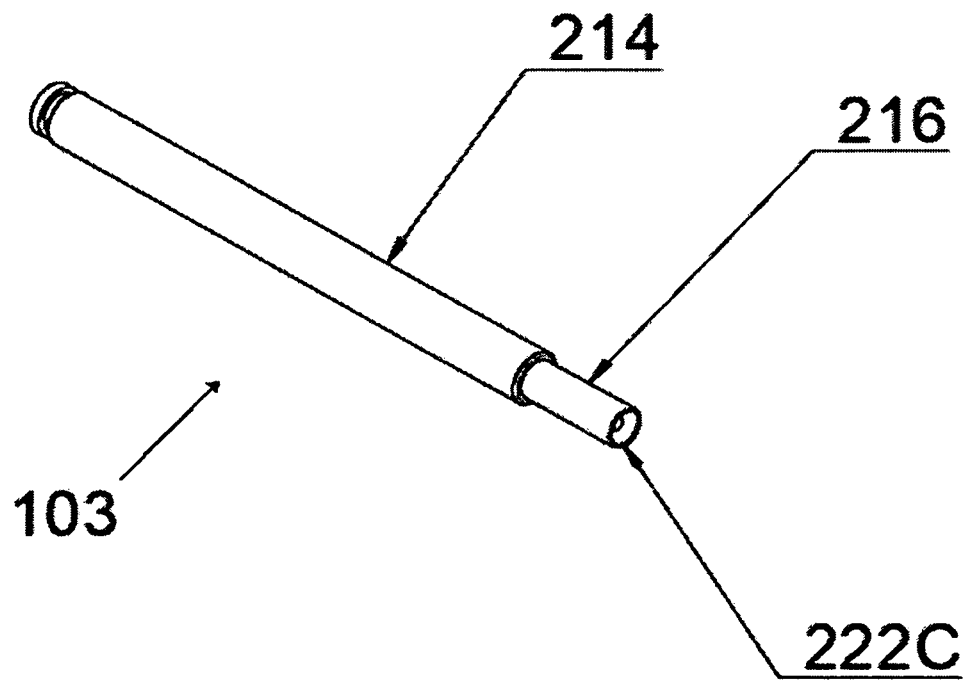
FIG. 5A is a perspective view of the probe shaft shown in FIGS. 2A-2D and FIGS. 4A-4D.
Figure 5B:
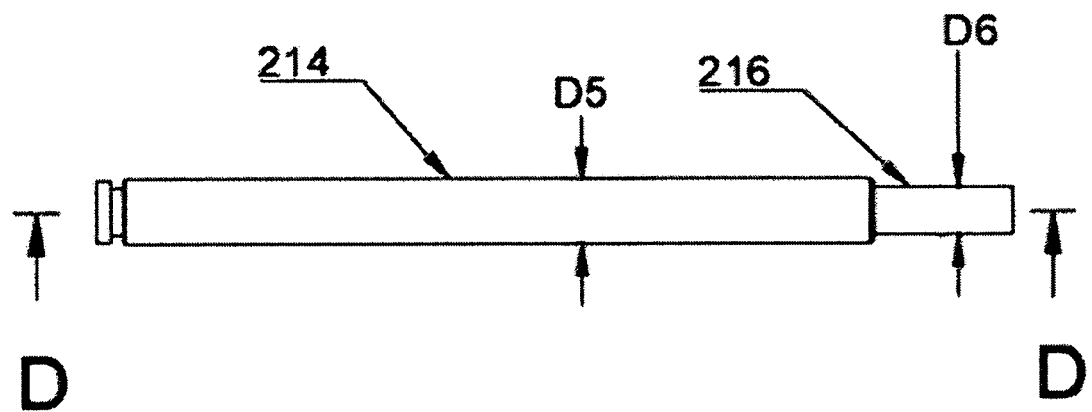
FIG. 5B is a side view of the probe shaft of FIG. 5A.
Figure 5C:
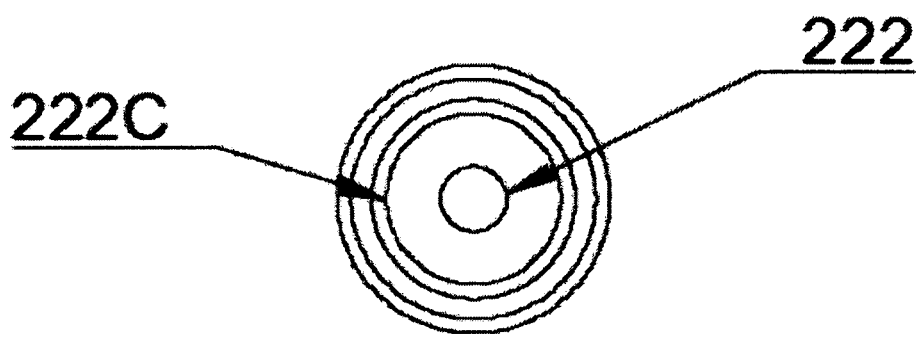
FIG. 5C is a front view of the probe shaft of FIG. 5A.
Figure 5D:
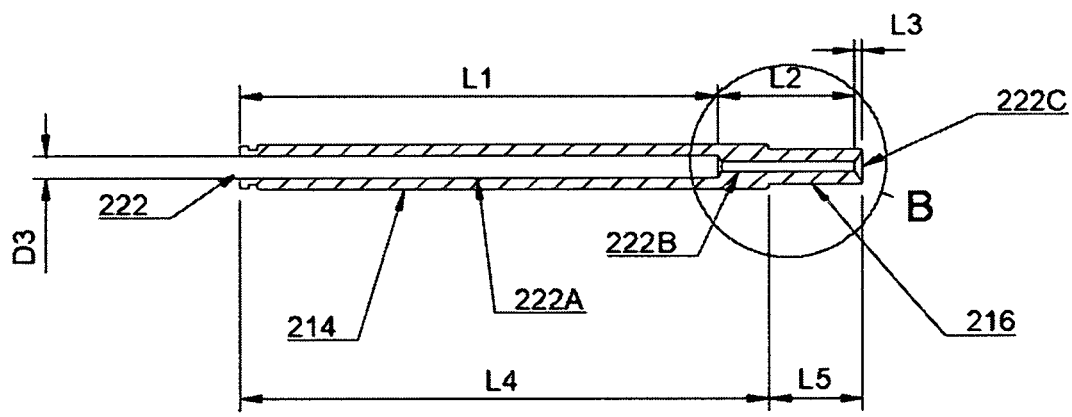
FIG. 5D is a cross sectional view of the probe shaft of FIG. 5B taken along line D-D in FIG. 5B.
Figure 5E:
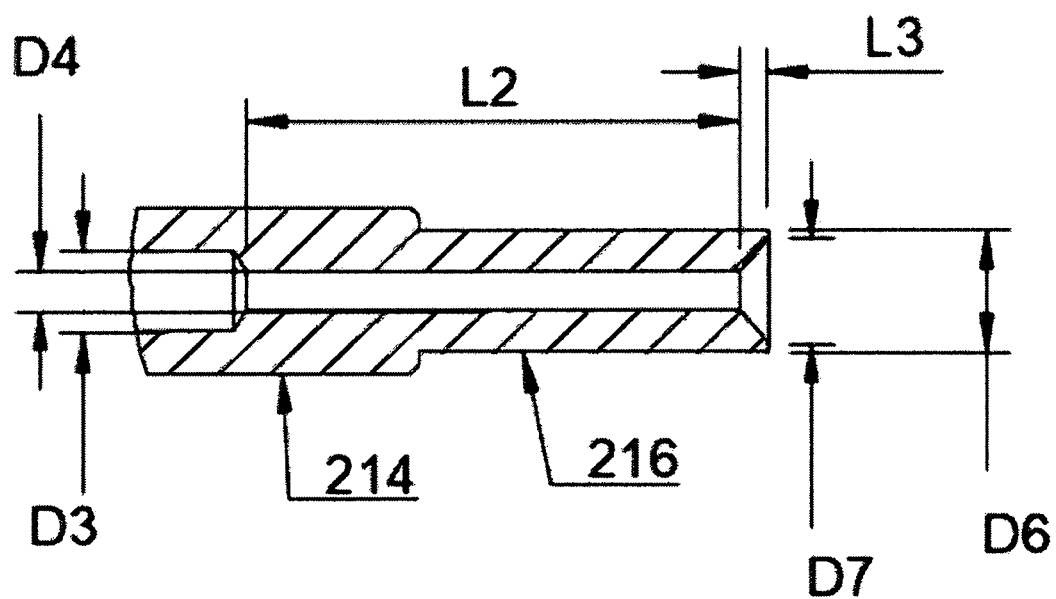
FIG. 5E is a magnification of the circled area B in FIG. 5D.

The probe tip and shaft assembly, shown, for example, in FIG. 2D, and composed of the probe tip 102 attached to the probe shaft 103, is shown all by itself in FIGS. 4A-4D. FIGS. 5A-5D show the details of the probe shaft 103 of the probe tip and shaft assembly shown in FIGS. 4A-4D. As shown in FIGS. 5A and 5D, the probe shaft 103 has a proximal end 214 and a distal end 216. The shaft 103 extends from inside the pressure chamber 202 through the distal end 206 of the housing 101 to the exterior of the probe 100. Proximal end 214 of the probe shaft 103 has an outside diameter D5 and distal end 216 of the probe shaft 103 has an outside diameter D6 smaller than D5. See FIG. 5B.

An axially directed concentric passage 222 alluded to above is formed in the shaft 103. The passage 222 has proximal and distal ends 224 and 226, respectively. The passage 222 is in communication with the air in the pressure chamber 202 at its proximal end 224. A passage in the tip 102 attached to the distal end of the shaft 103 is coaxial with the bore 222 and forms a jet or nozzle 213 shown, for example, in FIG. 2D. The nozzle 213 directs air originating from the pump 105 toward the eye 104.

The passage 222 in the probe shaft 103 is a specially shaped passage that reduces turbulence in the fluid flow through the probe 100 and thus smooths the fluid flow through the probe 100. The passage 222 efficiently passes energy without significant loss from the pneumatic fluid source 105 to the cornea of an eye 104 and the pressure detector 108. As shown most clearly in FIGS. 5A-5D, the passage 222 comprises at least three sections, (1) a proximal portion 222a extending a first predetermined length L1 from the proximal end of the shaft 103 along the axis of the shaft 103, (2) an intermediate portion 222b extending from distal end of the proximal portion 222a for a length L2 along the axis of the shaft 103, and (3) a distal portion 222c extending a length L3 along the axis of the shaft 103 from the distal end of the portion 222b to the distal end of the passage 222. The proximal portion 222a of the passage has constant diameter D3 less than the diameter D2 of the pressure chamber 202. The intermediate portion has a constant diameter D4 less than the diameter D3. The diameter of the distal portion of the probe shaft 103 increases from diameter D4 to a diameter D7, which is slightly less than the outer diameter D6 of the distal portion 216 of the shaft 103. The shaft 103 thus is an orifice tube 213 containing a passage 222 that forms a converging/diverging de Laval nozzle. This structure reduces turbulence in the airflow through the probe 100 and improves the performance of the probe 100.

The tip 102 has a cylindrical venting chamber 230 into which the orifice tube 213 extends. A circular flexible membrane 232 is stretched across the distal end of the orifice tube 213 and the open end of the venting chamber 230, thus sealing the orifice tube 213 and the venting chamber 230. Air flows from the fluid supply 105 to the pressure chamber 202, and then through the passage 222 in the shaft 103 and the orifice tube 213 toward the inner surface of the flexible membrane 232, which is placed in contact with an eye 104 to measure IOP. Vents 236 exhaust air from the venting chamber 230 when the pressure from the fluid supply 105 is sufficient to cause the membrane 232 to separate from the distal end of the orifice tube 213.

The flexible membrane 232 covering the open end of the probe tip 102 and the distal end of the orifice tube 213 encloses the venting chamber 230 to securely seal the venting chamber 230 and prevent extraneous leakage of air from the venting chamber. The membrane 232 comprises a circular portion 234 adapted to cover the open end of the probe tip 102 and a peripheral portion 238 adapted to wrap around the periphery of the probe tip 102 so as to secure the membrane 232 to the distal end of the probe tip 102. The flexible membrane may be made, for example, of silicone membrane sheeting fabricated using Class IV Silastic® Silicone available from Specialty Manufacturing, Inc. of Saginaw Mich. As most clearly shown in FIG. 6B, the probe tip 102 has a groove 240 around the periphery of the probe tip 102. The peripheral portion of the membrane 232 has a rib 242 adapted to enter the groove 240 in the probe tip 102 so as to secure the membrane 232 to the probe tip 102. The groove 240 has a distal sidewall 240a that is higher than the proximal sidewall 240b of the groove 240.

Figure 6A:
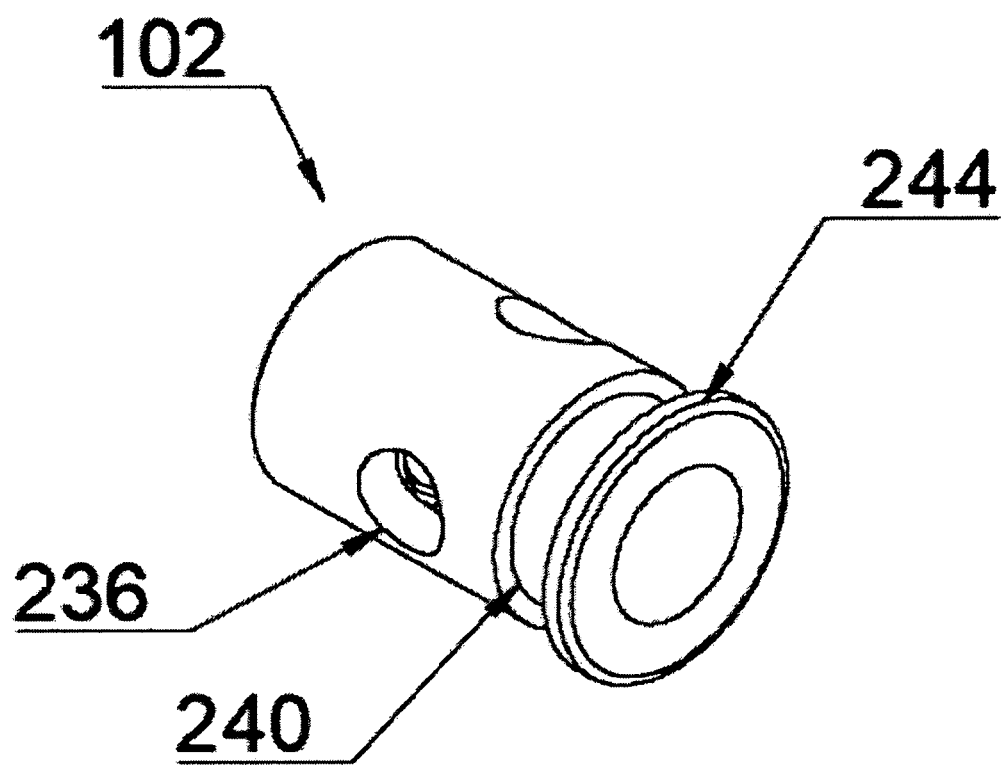
FIG. 6A is a perspective view of the probe tip shown in FIGS. 2A-2D and FIGS. 4A-4D.
Figure 6B:
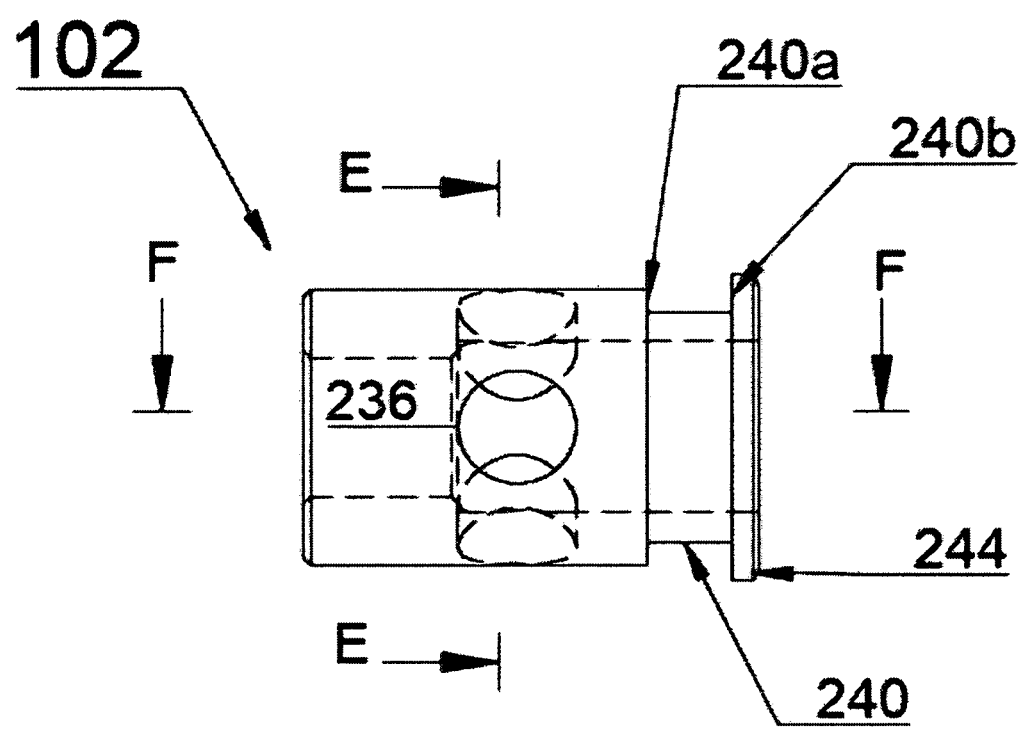
FIG. 6B is a side view of the probe tip of FIG. 6A.
Figure 6C:
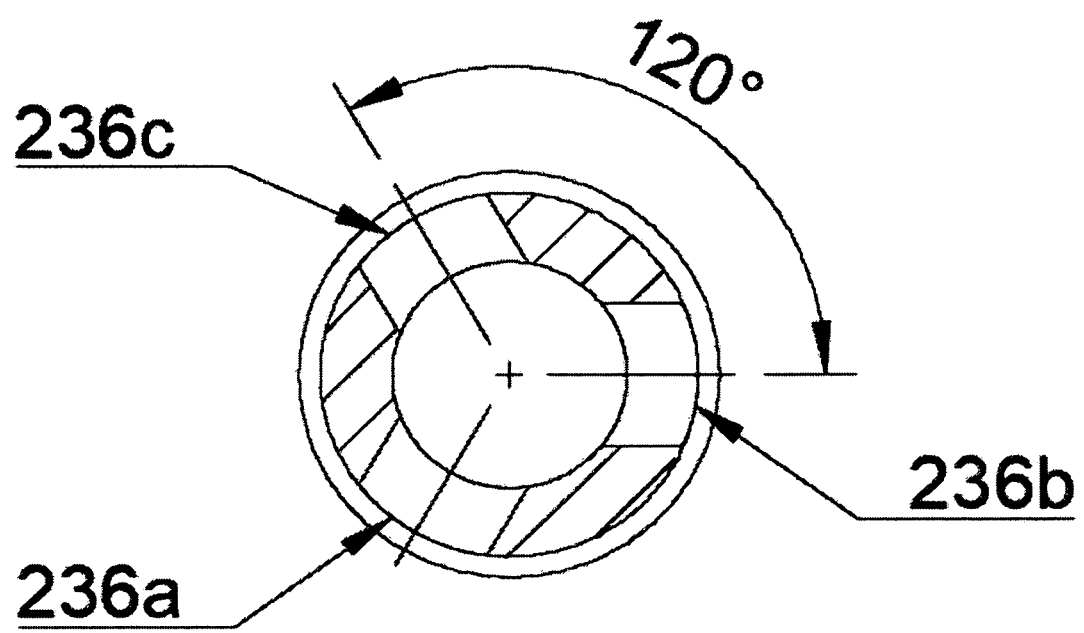
FIG. 6C is a cross sectional view of the probe tip of FIG. 6B taken along line E-E in FIG. 6B.
Figure 6D:
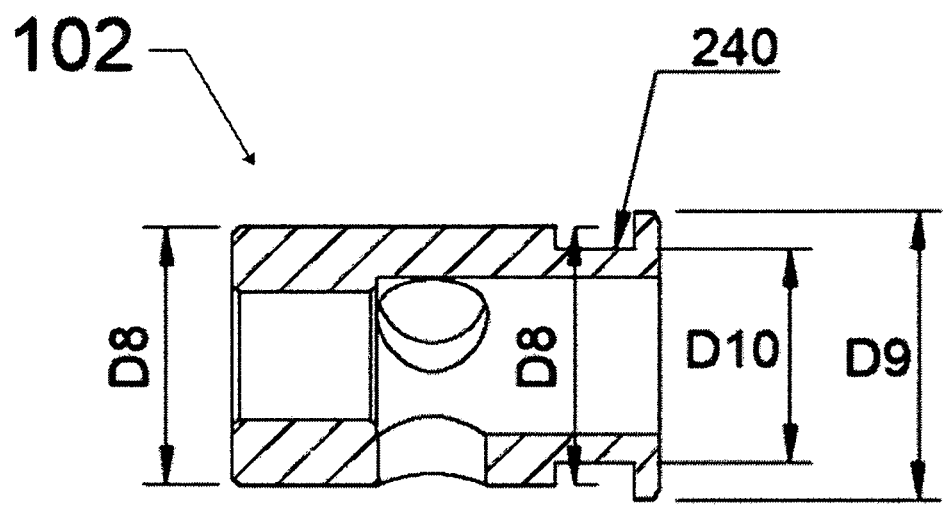
FIG. 6D is a cross sectional view of the probe tip of FIG. 6A taken along line F-F in FIG. 6B.

As shown most clearly in FIGS. 6A-6D, the probe tip 102 is generally cylindrical having an outside diameter D8. As shown in FIGS. 6B and 6D, a flange 244 having an outside diameter D9 is located on the distal end of the probe tip 102, where the diameter D9 is greater than the diameter D8. A groove 240 is formed between the flange 244 and the distal portion of the probe tip that has an outside diameter D8. The bottom of the groove has an outside diameter D10. The magnitude of the diameter D10 is less than magnitude of the diameter D8. The sidewalls 240a and 240b of the groove 240 thus are of unequal height. Due to the unequal height sidewalls 240a and 240b of the groove 240, when the membrane 232 is stretched across the opening in the probe tip 102, the aforementioned rib 242 shown, for example, in FIG. 10B, is rotated inwardly toward the sidewall 240a such that the distal corner or edge 242a of the rib 242 is urged against the back of the flange 244 and the proximal corner or edge 242b of the rib 242 is urged toward the bottom of the groove 240, thereby improving the seal of the membrane to the probe tip. All air introduced into the probe tip thus is exhausted only through the exhaust ports 236.

Figure 9A:
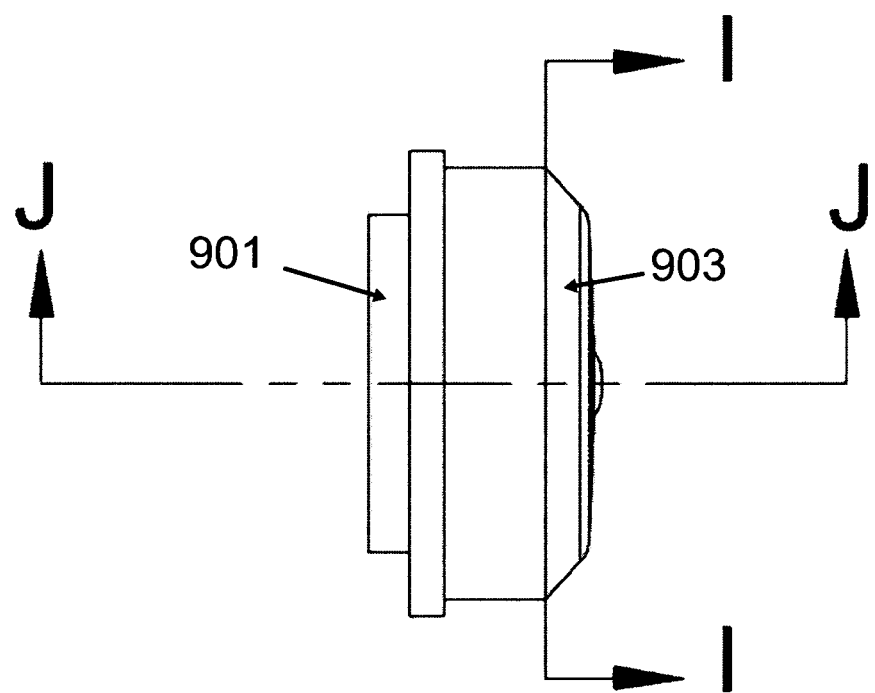
FIG. 9A is a side view of a prior art elastomeric cap on the distal end of a prior art probe tip.
Figure 9B:
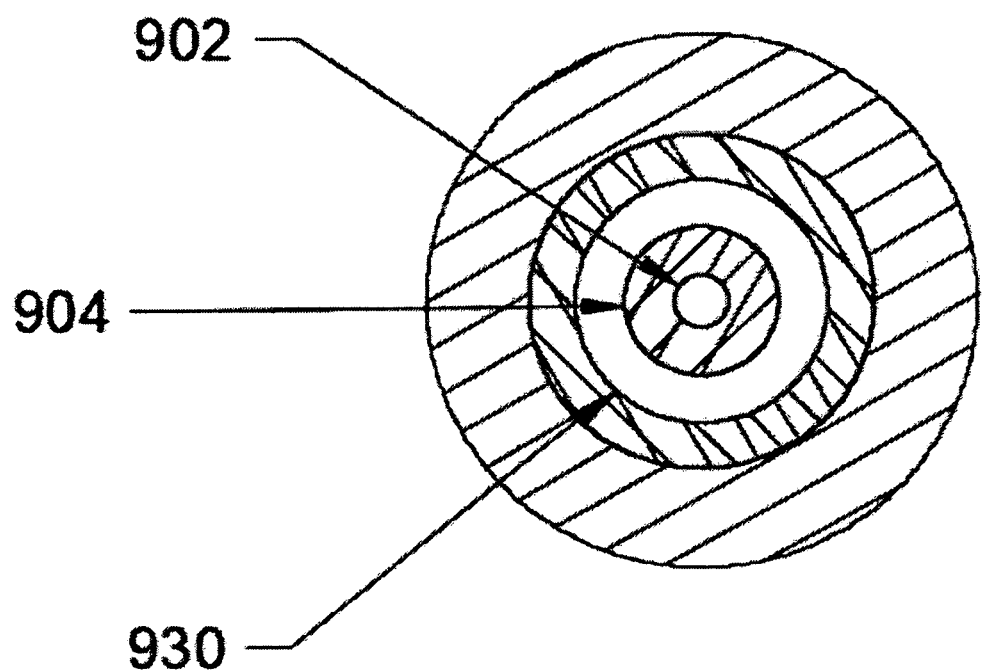
FIG. 9B is a cross sectional view of the cap and probe tip assembly shown in FIG. 9A taken along line I-I in FIG. 9A.
Figure 9C:
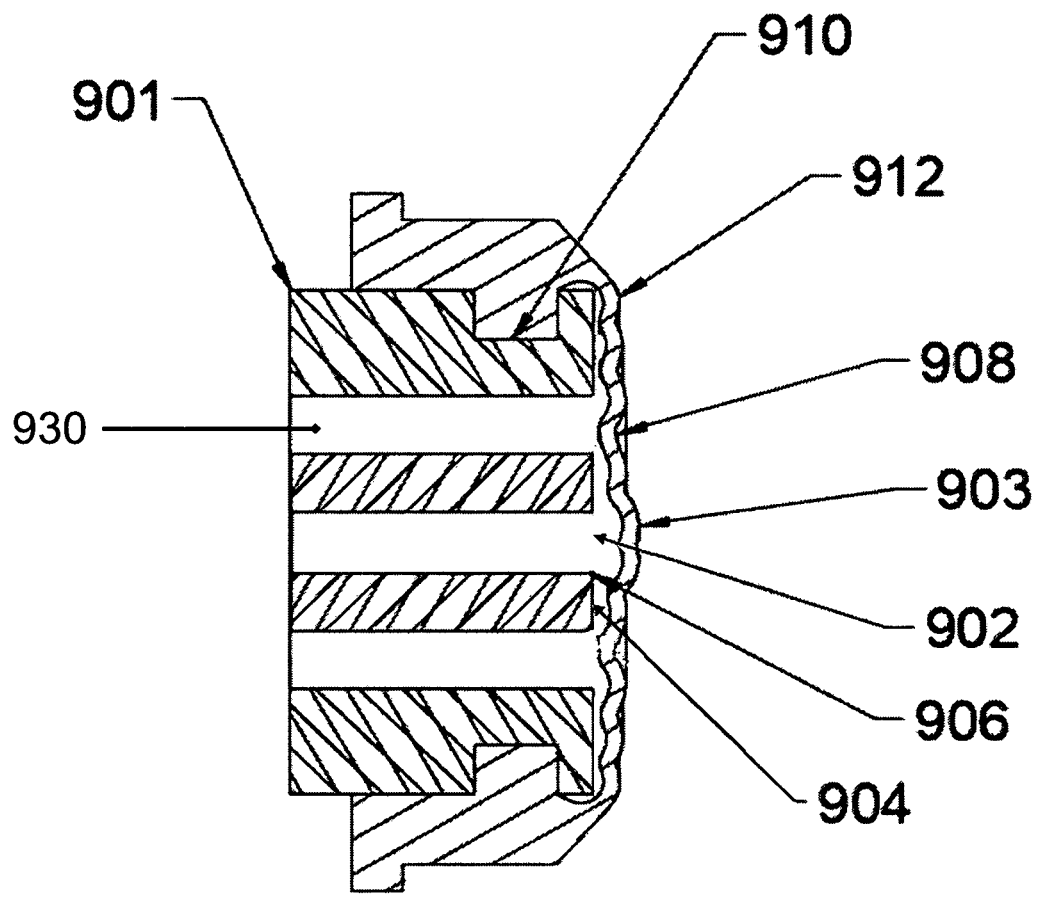
FIG. 9C is a cross sectional view of the cap and probe tip assembly of FIG. 9A taken along line J-J in FIG. 9A.

FIGS. 9A-9C show a representative prior design in cross section. Note the squared-off orifice 902 in a probe tip 901 covered by a flexible cap 903 in FIG. 9C that directs air across a wide annular surface 904 to a cylindrical venting chamber 930 with low velocity, resulting in turbulent flow and oscillation of the membrane covering the probe tip. The sharp inner edge 906 trips airflow. An audible "squeal" results, causing an unpredictable intermittent change in airflow and pressure at 908. Tight fitting slot at 910 resists seating, resulting in slack material across 912. Unpredictable and variable resistance to flow occurs at 902 as the loose membrane shifts and oscillates.

Figure 10A:
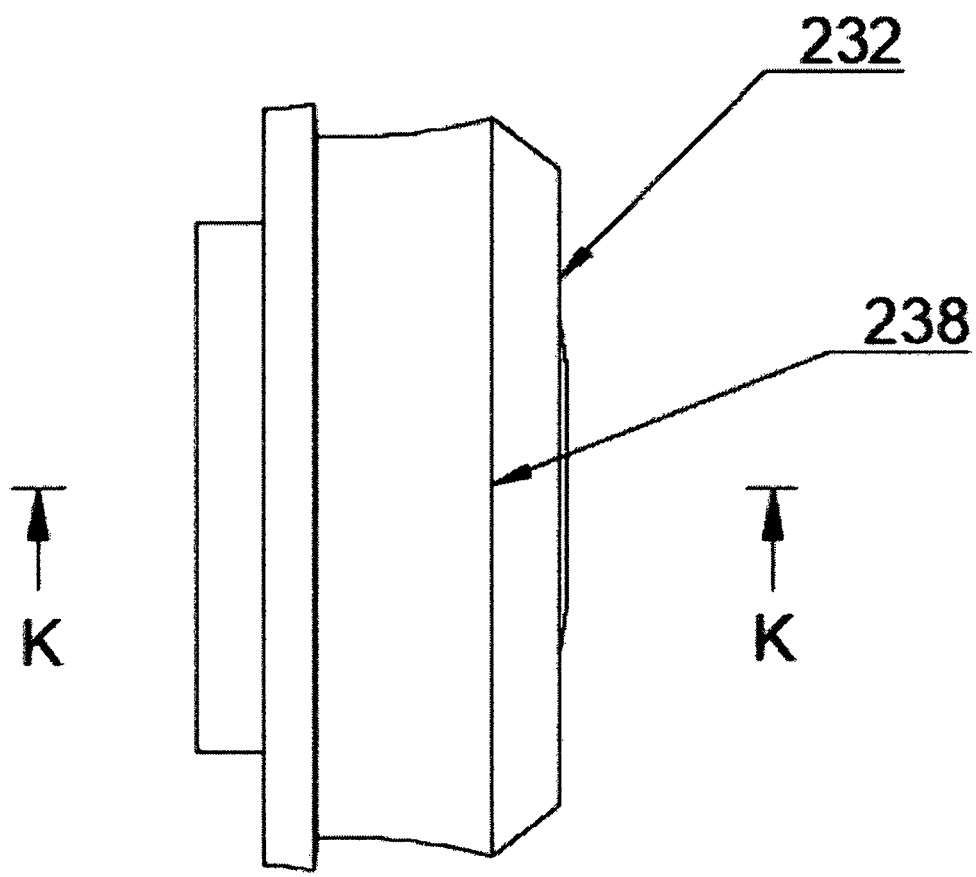
FIG. 10A is side view of an elastomeric cap and probe tip assembly in accordance with one example of the invention.
Figure 10B:
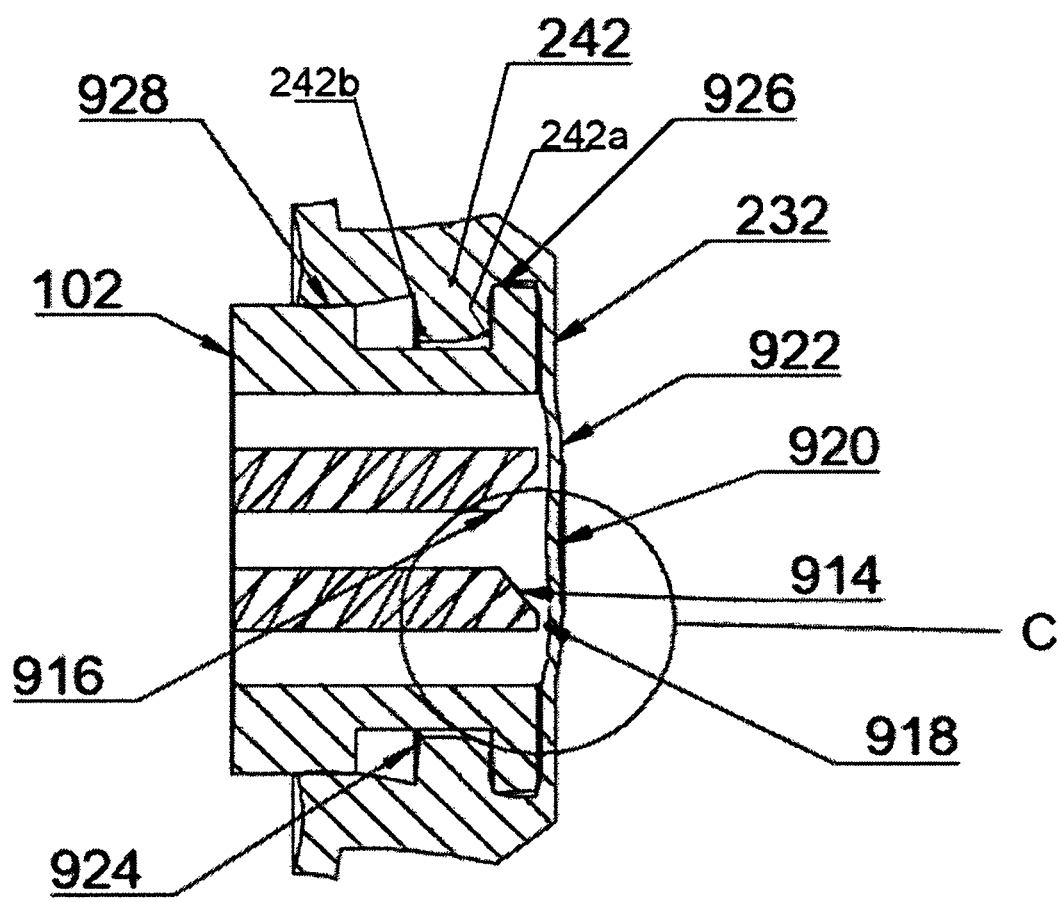
FIG. 10B is a cross sectional view of the cap and probe tip assembly shown in FIG. 10A taken along line K-K in FIG. 10A.
Figure 10C:
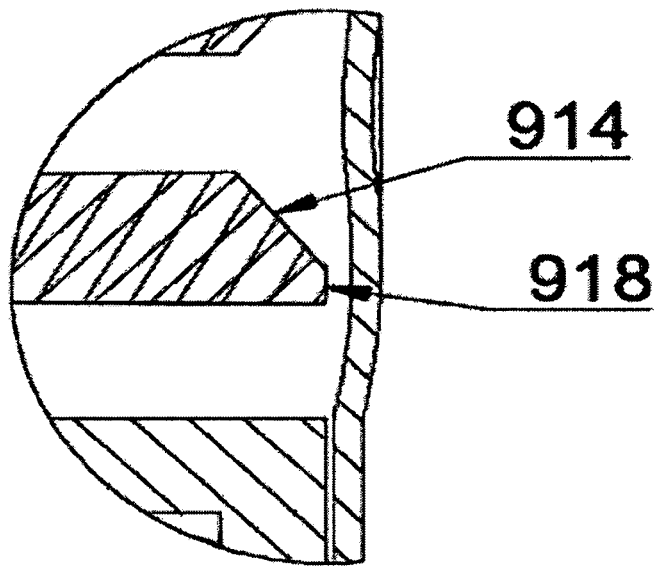
FIG. 10C is a magnified rendition of the area in circle C in FIG. 10B.

FIGS. 10A-10C show a cross section of a probe tip 102 designed in accordance with this invention. The tapered orifice 914 shown in FIGS. 10B and 10C ramps air progressively outward, resulting in non-turbulent flow and smooth displacement of membrane 232. The smooth, distally expanding, inner edge 916 guides stable, silent laminar airflow outward toward lip 918. Displacement of membrane 232 occurs in a narrow stable band at lip 918, resulting in a high differential pressure between annular areas 920 and 922 tending to stabilize membrane displacement at 920 and 922. Loose fitting slot at 924 with differential diameters at 926 and 928 allow inward and rearward tensioning motion of elastomeric membrane 232 across the probe tip. Constant, consistent, stable, and minimal resistance to airflow occurs.

The inventors sought to solve the problems with prior pneumatic tonometry devices, IOP analyzers, and ocular blood flow measurement devices by smoothing the fluid flow through the pressure probe used in those instruments, eliminating extraneous fluid leakages, and efficiently transferring energy from the pump 105 to the eye 104. The invention is advantageous for at least three main reasons.

First, the Rulon® bushing 218 substantially reduces friction experienced by the sliding probe shaft 103. At the same time, the bushing 218 is an effective seal against any air escaping around the probe shaft 103. None of the predicate devices have this feature; many used air bearings and claimed no substantial air loss, but this was not the case. In fact, there was an audible whistle noted by technicians during use of the predicate devices. The energy that would have otherwise been lost to the atmosphere is now more efficiently used to measure intraocular pressure.

Second, airflow inside the passageway 222 leading to the membrane 232 is laminar, while predicate devices experienced turbulent airflow because the back pressure from the probe tip 102 was interfering with the forward pneumatic fluid flow from pump 105. This is a major advantage as it reduces resistance to the air passing through the probe 100. The invention removes this one source of signal attenuation at the sensor 108.

Third, the tapered/chamfered surface 914 of the orifice 222 at the distal end facing the patient's eye creates a thin rim around the edge of the distal end of the probe shaft leaving no room for dynamic response. Predicate devices such as the Langham OBF and Paradigm probes had cylindrical shafts and a relatively wide annular surface at the end of the probe that produced high pitched, squealing and whistle-like sounds. This sound was another source of energy consumption, diverting energy that could be used to measure IOP. This further reduced signal level. The tapered design of this invention reduces the surface area of the central tube that interfaces with the membrane, and the area 918 that the air must travel to escape. This leads to a decreased Venturi effect between the probe and membrane surface, and thus little or no sound is produced, dramatically increasing the fidelity of the measurement.

As mentioned above, the pressure probe 100 described here is particularly useful in a composite ocular blood flow analyzer (COBFA), described, for example, in aforementioned published patent application US2017/0245751A1.

The pressure probe used in a COBFA is distinctly different from the pressure probe used in a traditional pneumatic tonometer, pioneered by Maurice Langham PhD, as described, for example, in Langham U.S. Pat. No. 4,883,056. The various pneumatic tonometers that have been cleared by the FDA, marketed, and sold in the USA and abroad were at the time cutting edge technology, but are no longer so cutting edge.

Specific Example of the Invention

Dimensional details of a specific example of the invention are summarized in the Table 1 below:

TABLE 1

| Reference Numeral | Description | Representative Dimension |
|---|---|---|
| D1 | Outside diameter of the probe housing 101 | 0.453 inches |
| D2 | Inside diameter of the pressure chamber 202 | 0.266 inches |
| D3 | Inside diameter of the proximal portion 222a of the passage 222 through probe shaft 103 | 0.048 inches-0.060 inches |
| D4 | Inside diameter of the intermediate portion 222b of the passage 222 through the probe shaft 103 | 0.023-0.028 inches |
| D5 | Outside diameter of the proximal portion 214 of the probe shaft 103 | 0.10000 inches-0.10025 inches |
| D6 | Outside diameter of the distal portion 216 of the probe shaft 103 | 0.072 inches-0.080 inches |
| D7 | Maximum diameter of the flared portion 222c of the passage 222 through the probe shaft 103 | 0.063 inches |
| D8 | Outside diameter of the probe tip 102 | 0.193 inches |
| D9 | Outside diameter of the flange 244 at the distal end of the probe tip 102 | 0.215 inches |
| D10 | Outside diameter of the bottom of the groove 240 on the probe tip 102 | 0.161 inches |
| L1 | Longitudinal length of proximal portion 222a of the passage 222 through the probe shaft 103 | 0.95-1.0 inches |
| L2 | Longitudinal length of the intermediate portion 222b of the passage 222 through the probe shaft 103 | 0.27-0.30 inches |
| L3 | Longitudinal length of the flared portion 222c of the passage 222 through the probe shaft 103 | 0.015 inches |
| L4 | Length of the proximal portion 214 of the probe shaft 103 | 1.06 inches |
| L5 | Length of the distal portion 216 of the probe shaft 103 | 0.2 inches |

A pneumatic tonometer in accordance with this invention has a cylinder with an air inlet at the rear and a central piston extending from the front of the unit. Air entering the rear of the cylinder pushes on the piston. This pressure is limited by air escaping through the piston via a passage of approximately 0.060" in diameter extending about 1.0" from the rear to within approximately 0.30" of the front, where it continues through narrower passage having a diameter of about 0.028 inches for the remaining approx. 0.30". The final 0.015" of the 0.028" diameter section flares outward to create a bugle like exit orifice. This flare is rimmed with an approximately 0.015" wide flat rim extending from the largest diameter of the flare to nearly the outer diameter of the piston. In the configuration above, a central hole in the piston prevents the piston from executing a hard thrust outward.

The central hole in the piston faces the eye, and comes in contact with the cornea (through a soft protective cover). The air escapes then only when the cornea flattens against the outward pressure of the eye, an amount commensurate with the geometry of the probe tip. In this condition, a limited flow of air escapes, maintaining cylinder pressure at a fixed proportion to the internal pressure of the opposing eye.

The forces involved are very small. So small that friction between the cylinder and the piston at the bushing becomes a major factor. Equilibrium between LOP and probe pressure will not occur unless this friction is extremely low, not tangible to the hand. A test is to move the cylinder to a vertical position, so that the piston can extend or retract under gravity. A free motion indicates a low friction state, friendly to successful operation of the tonometer. Since normal precision-machined parts have tolerances too great to ensure consistent low friction, the designs to date have allowed excess slop or wide tolerances between the cylinder and the piston. The piston so mounted will frequently bind in the cylinder as it slides, preventing consistent proper operation of the device.

When there is slop in the piston cylinder interface (estimated to be approximately 0.002" measured as a difference in radius between the two curved surfaces), air has an undesirable escape path out of the cylinder. This volume of air is lost in establishing equilibrium between the eye and the cylinder pressure. Since the pulsation of pressure being measured is very small, any leak represents a significant loss of pressure before the pulsations can reach a pressure sensor connected to the cylinder. This clips the max probe pressure pulse response to the eye by 20% or more as shown by experiments in which parallel measurements were made, one with the slip joint, one without.

Resistance to flow in thin tubes is proportional to length, and to a much greater degree, diameter. The outlet area of the outlet hole in the piston equates to approximately 0.00615 square inches. The clearance of 0.002" inch equates to approx. 0.000478 square inches, or 77.77% of the piston hole area. A volume of air is bled off through the clearance tolerance, according to the formula for flow through thin tubes. This volume is not calculable using standard tube equation, but is likely to be significant and highly variable as the piston shifts, occluding the passage. The air escaping along the desired path, past the cornea surface, supports sensing pressure variations that are then converted to IOP pulsations. Air escaping through the clearance around the piston is not sensed, it represents a loss of measurement of some portion of each pulse.

Since IOP without the pulse component is calculated using a known difference between probe pressure and IOP, air loss is to some extent compensated for in this calculation, although since at different probe pressures different amounts of leakage will occur, this leakage does affect the otherwise linear relationship between probe pressure and IOP. It is probable it has a much greater effect on sensing small pulsations of pressure in the eye, preventing the probe pressure over time from achieving a peak proportionate to the peak of the IOP during each pulse. This latter is born out by the experiment in which a 20% to 30% loss of probe pressure occurs when the leak is present, increasing at higher probe pressures.

Many factors cause constant shift of flow between the desired path and the clearance between piston and cylinder. This is a regular occurrence in prior art tonometers. The resulting oscillation is audible, in the order of 80 Decibels SPL at frequencies from primarily from 400 to 12K hertz. As a factor in performance, the "squeal" of the old tonometers is mistakenly welcomed by users because they believe that the "squeal" tends to indicate more reproducible measurements.

Because the "squeal" has highly variable interdependent causative factors, it can occur, or not, even when measuring the same eye twice in the same exam. A significant drop in pressure readings is frequently visible in the comparative results when the squeal is present. In addition, this difference in pressure readings is not linear across pressure ranges. Plots of probe pressure vs. IOP values in prior art devices when the "squeal" is present show significant non-linearity, including areas in certain pressure ranges of near total unresponsiveness, or much diminished response. The above audible squeal has some additional negatives. Primarily it is not reproducible, occurring at some IOPs and not others, and or not occurring at all. This indicates a fidelity loss associated with the squeal that could adversely impact LOP pulse detection accuracy and sensitivity in the prior art tonometry devices. The above errata caused many users to report they found the prior art machine unusable or unacceptable. The only solution is to limit or eliminate the "squeal" by reducing or eliminating the air loss imbalance.

In general, oscillation occurs when forces are not balanced across a pivot or center of motion, and some variability causes dynamic feedback. Shifting the balance of airflow largely to the desired path, namely, to a direct path from the pressure chamber 202 through the passage 222 and nozzle 213 to the cornea, will lessen or eliminate the oscillation and feedback.

An improved design of a plastic bushing between the piston and cylinder results in a much smaller, reproducible clearance. This is adjustable in the field as well, so wear and tolerance creep can be eliminated. These occur very quickly in prior art machines due to the very small surface areas involved, a higher coefficient of friction, and the relatively large sliding motion.

A further contribution to instability leading to an audible squeal is in the prior art cornea/instrument area of contact. The probe sequence of large to small and then bugle shaped outlet orifices in this invention, guide the outflow to eliminate or reduce the negative stability of this airflow. The primary orifice at the cornea is approximately 0.028" diameter, and approximately 0.00615 square inches. The clearance reduction of 0.0005" may effectively increase the resistance to outflow to near zero, a small single digit percentage of total outflow from a possible 20% or more. Regardless of the exact numbers, the balance of forces between the intended outlet and the clearance leak is shifted heavily in favor of the former. Oscillation is highly unlikely in the new design, versus certain and intermittent in the prior art.

In prior art devices the change in IOP caused by the probe itself touching the eye was carefully studied. It is reported in literature as +1.8 mmHg. This gain is presumably due to the pressure the probe exerts on the eye, pressure needed to overcome forces that are not fully understood. These seem to be linked to the amount of air loss tolerated in the prior art probes. Once this air loss is corrected as in the devices in accordance with this invention, contact effect on IOP is typically 0.6 mmHg. This suggests that the air loss in prior art demanded a higher input of energy to maintain probe pressure. This energy may contribute to pressure on the eye incidental to probe contact. In any case, the new probe is significantly more responsive to pressure pulsation in the eye, while placing less pressure on the object being measured. It seems these things may be linked, as any pressure imposed on the eye would likely tend to suppress pulsation.

There remain no clear technical barriers to widespread use of this valuable instrument. Most of these things in retrospect seem intuitive or individually rather trivial. In fact they were subtle and very difficult to trace to a cause, such that prior persons skilled in the art who were highly qualified to analyze the instrument performance did not identify them in spite of known performance issues.

Together the new bushing design and material, and the advanced airflow guide or de Laval style orifice in the piston tip, reduces or eliminates turbulence, friction, air loss, and a "squeal". These are now insignificant factors in devices in accordance with this invention. This advances the pneumatic tonometer from a uniquely useful but quirky research device to a mainstream tool. It is now useful to technicians without special knowledge or extensive experience. The tonometer can now be successfully used in the limited time available during a patient eye exam as compared with the greater time available in a research experiment.

CONCLUSION

The Title, Technical Field, Background, Summary, Brief Description of the Drawings, Detailed Description, and Abstract are meant to illustrate the preferred embodiments of the invention and are not in any way intended to limit the scope of the invention. The scope of the invention is solely defined and limited in the claims set forth below.

The invention claimed is:

1. A probe shaft adapted to be used in a pneumatic tonometer, comprising:
   a convergent/divergent nozzle adapted to receive pressurized pneumatic fluid from a pressure chamber and to direct the received pressurized pneumatic fluid to an eye to measure intraocular pressure.

2. A tonometric pressure probe, comprising:
   an elongated housing enclosing a cylindrical pressure chamber, the pressure chamber having a predetermined inside diameter and adapted to receive pressurized pneumatic fluid from a pressure source; and
   a cylindrical elongated probe shaft as defined in claim 1 extending from the pressure chamber through the housing.

3. The tonometric pressure probe of claim 2, in which the nozzle has a longitudinal cylindrical passage having a predetermined diameter extending through the nozzle, the passage comprising in series a first portion in which the inside diameter of the passage decreases as a function of distance from a proximal end of the passage, and a second portion in which the inside diameter of the passage increases as a function of distance from the proximal end of the passage.

4. The tonometric pressure probe of claim 2, in which the nozzle has a cylindrical passage longitudinally extending through the nozzle, the passage comprising a proximal portion of length L1, an intermediate portion of length L2, and a distal portion of length L3, the proximal portion having a diameter D3 that is less than the inside diameter of the pressure chamber, the intermediate portion having a diameter D4 that is less than diameter D3, and the distal portion having a flared diameter beginning with diameter D4 at a proximal end of the distal portion, the diameter of the distal portion gradually increasing to a diameter D7 that is less than an outside diameter D6 of the nozzle to thereby form a radially directed flat rim around the distal end of the nozzle.

5. The tonometric pressure probe of claim 2, further comprising:
a low coefficient of friction polytetrafluoroethylene (PTFE) bushing that seals one end of the housing, the probe shaft extending through a cylindrical passage in the bushing, and the bushing forming a linear bearing permitting the probe shaft to axially slide into and out of the pressure chamber without any substantial leakage of pneumatic fluid from the pressure chamber.

6. The tonometric pressure probe of claim 2, further comprising:
a cylindrical probe tip having an open end, the probe tip being connected to one end of the probe shaft, the probe tip comprising a groove around a periphery of the probe tip, the groove having a bottom surface, a proximal sidewall having a first height, and a distal sidewall having a second height, the second height being greater than the first height; and
a flexible membrane covering the open end of the probe tip, the membrane comprising a radially extending circular portion that seals the open end of the probe tip and a peripheral portion that wraps around the periphery of the probe tip and extends across the groove around the periphery of the probe tip, the flexible membrane having a rib with proximal and distal corners that enter the groove, the differing height sidewalls causing the proximal corner of the rib to be urged toward the bottom surface of the groove and the distal corner of the rib to be urged toward the distal sidewall of the groove.

7. The tonometric pressure probe of claim 5, further comprising:
a cylindrical probe tip having an open end, the probe tip being connected to one end of the probe shaft, the probe tip comprising a groove around a periphery of the probe tip, the groove having a bottom surface, a proximal sidewall having a first height, and a distal sidewall having a second height, the second height being greater than the first height; and
a flexible membrane covering the open end of the probe tip, the membrane comprising a radially extending circular portion that seals the open end of the probe tip and a peripheral portion that wraps around the periphery of the probe tip and extends across the groove around the periphery of the probe tip, the flexible membrane having a rib with proximal and distal corners that enter the groove, the differing height sidewalls causing the proximal corner of the rib to be urged toward the bottom surface of the groove and the distal corner of the rib to be urged toward the distal sidewall of the groove.

8. A low coefficient of friction PTFE bushing adapted to be used in a pneumatic tonometer comprising:
a threaded portion and a conical slanted portion adapted to be received by corresponding threaded and slanted portions of a housing enclosing a tonometric pressure chamber that supplies pneumatic fluid to measure intraocular pressure, receipt of the threaded and the slanted portions of the bushing by the threaded and slanted portions of the housing thereby sealing the pressure chamber; and
a cylindrical passage through the PTFE bushing, the cylindrical passage adapted to receive and radially squeeze a hollow tonometric probe shaft so as to prevent pneumatic fluid from escaping the pressure chamber around the probe shaft and to allow axial motion of the probe shaft into and out of the pressure chamber.

9. A tonometric pressure probe, comprising:
a housing comprising an elongated cylindrical pressure chamber adapted to receive pressurized pneumatic fluid;
a hollow probe shaft adapted to receive pressurized pneumatic fluid from the pressure chamber and to direct the received pressurized pneumatic fluid to an eye to measure intraocular pressure; and
the low coefficient of friction PTFE bushing of claim 8 sealing the pressure chamber, the hollow shaft extending from the pressure chamber through the cylindrical passage in the PTFE bushing.

10. The tonometric pressure probe of claim 9, in which the housing comprises a threaded female section and a conical slanted female section, and the bushing comprises a threaded male section and a conical slanted male section, the slanted sections adapted to press against one another when the bushing is screwed into the housing so as to increase radial squeezing of the shaft at the axial position of the conical sections, the amount of increased radial squeezing being dependent on how tightly the bushing is screwed into the housing.

11. A cylindrical probe tip adapted to be placed against a cornea to measure intraocular pressure, comprising:
a cylindrical probe tip having two end faces and a curved peripheral surface connecting the two end faces, one of the faces being open to provide an exhaust chamber that releases pneumatic fluid that applies force to the cornea, the other of the two end faces adapted to receive one end of a probe shaft carrying pneumatic fluid toward the cornea;
the probe tip further comprising a groove formed around the peripheral surface of the cylindrical probe tip, the groove having a bottom surface, a proximal sidewall, and a distal sidewall, the height of the distal sidewall being greater than the height of the proximal sidewall, the groove adapted to receive a rib formed on the inside surface of an elastomeric cap that seals the open end of the cylindrical probe tip, the differing height sidewalls adapted to urge the rib toward the bottom surface and distal sidewall of the groove.

12. A tonometric pressure probe, comprising:
a hollow elongated housing defining a pressure chamber inside the housing;
a probe shaft extending from inside the pressure chamber to outside the pressure chamber through the housing; and
the cylindrical probe tip of claim 11 attached to the probe shaft.

13. The tonometric pressure probe of claim 2, further comprising:

pressurized pneumatic fluid supply adapted to supply pressurized pneumatic fluid to the pressure chamber at a substantially constant flow rate.

14. The tonometric pressure probe of claim 9, in which the hollow probe shaft contains a longitudinal passage through the shaft that forms a converging/diverging de Laval nozzle.

15. The tonometric pressure probe of claim 10, in which the hollow probe shaft contains a longitudinal passage through the shaft that forms a converging/diverging de Laval nozzle.

16. The tonometric pressure probe of claim 12, in which the hollow probe shaft contains a longitudinal passage through the shaft that forms a converging/diverging de Laval nozzle.

17. The tonometric pressure probe of claim 5, in which the PTFE material is Rulon® brand PTFE material.

18. The tonometric pressure probe of claim 17, in which the PTFE material is Rulon® brand No. 641 medical grade PTFE material.

19. The tonometric pressure probe of claim 4, further comprising:

a low coefficient of friction polytetrafluoroethylene (PTFE) bushing that seals one end of the housing, the probe shaft extending through a cylindrical passage in the bushing, and the bushing forming a linear bearing permitting the probe shaft to axially slide into and out of the pressure chamber without any substantial leakage of pneumatic fluid from the pressure chamber;

in which the housing comprises a threaded female section and a conical slanted female section, and the bushing comprises a threaded male section and a conical slanted male section, the slanted sections adapted to press against one another when the bushing is screwed into the housing so as to increase radial squeezing of the shaft at the axial position of the conical sections, the amount of increased radial squeezing being dependent on how tightly the bushing is screwed into the housing.

20. The tonometric pressure probe of claim 19, further comprising:

a cylindrical probe tip having an open end, the probe tip being connected to one end of the probe shaft, the probe tip comprising a groove around a periphery of the probe tip, the groove having a bottom surface, a proximal sidewall having a first height, and a distal sidewall having a second height, the second height being greater than the first height; and a flexible membrane covering the open end of the probe tip, the membrane comprising a radially extending circular portion that seals the open end of the probe tip and a peripheral portion that wraps around the periphery of the probe tip and extends across the groove around the periphery of the probe tip, the flexible membrane having a rib with proximal and distal corners that enter the groove, the differing height sidewalls causing the proximal corner of the rib to be urged toward the bottom surface of the groove and the distal corner of the rib to be urged toward the distal sidewall of the groove.

21. A flexible membrane adapted to seal an open end of an elongated pneumatic tonometric probe tip, the elongated pneumatic tonometric probe tip having an end portion and a peripheral portion, the flexible membrane comprising:

a radially extending end portion that seals an open end portion of a probe tip;

a peripheral portion that wraps around a periphery of the probe tip and extends across a groove formed around the peripheral portion of the probe tip, the groove having a bottom surface, a proximal sidewall having a first height, and a distal sidewall having a second height, the second height being greater than the first height; and the flexible membrane having a rib with proximal and distal corners that enter the groove when the flexible membrane is attached to the open end of the elongated pneumatic tonometric probe tip, the differing height sidewalls causing the proximal corner of the rib to be urged toward the bottom surface of the groove and the distal corner of the rib to be urged toward the distal sidewall of the groove to thereby seal the end portion of the elongated pneumatic tonometric probe tip.

* * * * *